(12) United States Patent
Davies

(10) Patent No.: US 12,035,964 B2
(45) Date of Patent: *Jul. 16, 2024

(54) ELECTROSURGICAL PERICARDIAL PUNCTURE

(71) Applicant: Boston Scientific Medical Device Limited, Ballybrit (IE)

(72) Inventor: Gareth Davies, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 888 days.

This patent is subject to a terminal disclaimer.

(21) Appl. No.: 16/939,264

(22) Filed: Jul. 27, 2020

(65) Prior Publication Data

US 2020/0352647 A1 Nov. 12, 2020

Related U.S. Application Data

(63) Continuation-in-part of application No. 16/124,684, filed on Sep. 7, 2018, now Pat. No. 11,298,184, which
(Continued)

(51) Int. Cl.
*A61B 18/18* (2006.01)
*A61B 8/00* (2006.01)
(Continued)

(52) U.S. Cl.
CPC ........ *A61B 18/1492* (2013.01); *A61B 8/0841* (2013.01); *A61B 8/0883* (2013.01);
(Continued)

(58) Field of Classification Search
CPC ............ A61B 17/2202; A61B 17/3478; A61B 18/1492; A61B 18/1815;
(Continued)

(56) References Cited

U.S. PATENT DOCUMENTS 5,056,526 A * 10/1991 Khalil .................... A61B 5/352
600/526
5,385,156 A * 1/1995 Oliva .................... A61F 2/2481
128/898
(Continued)

OTHER PUBLICATIONS

Eduardo Sosa, Mauricio Scanavacca, Andre D'Avila, Flavio Oliveira, Jose Antonio F. Ramires, "Nonsurgical transthoracic epicardial catheter ablation to treat recurrent ventricular tachycardia occurring late after myocardial infarction", "Journal of the American College of Cardiology", May 2000, pp. 1442-1449, vol. 35, No. 6, Publisher: Elsevier Science Inc., Published in: US.
(Continued)

*Primary Examiner* — Michael F Peffley
*Assistant Examiner* — Amanda L Zink
(74) *Attorney, Agent, or Firm* — Nelson Mullins Riley & Scarborough LLC

(57) ABSTRACT

Devices and methods for providing access to the pericardial cavity while reducing risk of myocardial damage. One method comprises the steps of: (a) advancing a puncture device towards a heart, the puncture device including an energy delivery device at a distal end of the puncture device; (b) delivering a single pulse of a pulsed energy through the energy delivery device to a parietal pericardium of the heart to create a void relatively close to the energy delivery device while maintaining the distal end of the puncture device in a substantially stationary position relative to the parietal pericardium; (c) advancing the puncture device a short distance into the void; (d) checking if the puncture device has accessed the pericardial cavity by measuring pressure on the distal end of the puncture device; and (e) repeating steps (b), (c), and (d), if necessary, until the energy delivery device is located at least partially within the pericardial cavity. The methods may include a step of confirming that the puncture device is at least partially within the parietal cavity by
(Continued)

injecting or aspirating fluid through a lumen in the puncture device or measuring the pressure or electrical impedance at the distal end of the puncture device.

18 Claims, 12 Drawing Sheets

Related U.S. Application Data is a continuation of application No. 14/933,356, filed on Nov. 5, 2015, now Pat. No. 10,166,070, which is a continuation-in-part of application No. 14/257,053, filed on Apr. 21, 2014, now Pat. No. 9,179,932, which is a continuation-in-part of application No. 13/656,173, filed on Oct. 19, 2012, now Pat. No. 8,702,692, which is a continuation-in-part of application No. 12/005,316, filed on Dec. 27, 2007, now Pat. No. 8,308,720.

(51) Int. Cl.
| | |
|---|---|
| *A61B 8/08* | (2006.01) |
| *A61B 8/12* | (2006.01) |
| *A61B 17/34* | (2006.01) |
| *A61B 18/14* | (2006.01) |
| *A61B 90/00* | (2016.01) |
| *A61B 17/00* | (2006.01) |
| *A61B 17/22* | (2006.01) |
| *A61B 18/00* | (2006.01) |

(52) U.S. Cl.
CPC ............... *A61B 8/12* (2013.01); *A61B 8/445* (2013.01); *A61B 8/4494* (2013.01); *A61B 8/481* (2013.01); *A61B 17/3478* (2013.01); *A61B 90/37* (2016.02); *A61B 2017/00026* (2013.01); *A61B 2017/00154* (2013.01); *A61B 2017/00243* (2013.01); *A61B 2017/00247* (2013.01); *A61B 2017/00353* (2013.01); *A61B 2017/22014* (2013.01); *A61B 17/2202* (2013.01); *A61B 2018/00083* (2013.01); *A61B 2018/00291* (2013.01); *A61B 2018/00363* (2013.01); *A61B 2018/00601* (2013.01); *A61B 2018/00702* (2013.01); *A61B 2018/00839* (2013.01); *A61B 2018/00875* (2013.01); *A61B 2018/1861* (2013.01); *A61B 2090/064* (2016.02); *A61B 2090/378* (2016.02)

(58) Field of Classification Search
CPC .......... A61B 2017/00026; A61B 2017/00084; A61B 2017/00154; A61B 2017/00243; A61B 2017/00247; A61B 2017/00353; A61B 2017/22014; A61B 2018/00083; A61B 2018/00196; A61B 2018/00291; A61B 2018/00363; A61B 2018/00577; A61B 2018/00601; A61B 2018/00702; A61B 2018/00708; A61B 2018/00791; A61B 2018/00839; A61B 2018/00875; A61B 2018/00982; A61B 2018/00994; A61B 2018/1475; A61B 2018/167; A61B 2018/1861; A61B 2090/064; A61B 2090/376; A61B 2090/378; A61B 2090/3925; A61B 2090/3966; A61B 2562/0247; A61B 6/12; A61B 8/0841; A61B 8/0883; A61B 8/12; A61B 8/445; A61B 8/4455; A61B 8/4494; A61B 8/481; A61B 90/37

See application file for complete search history.

(56) References Cited

U.S. PATENT DOCUMENTS

| | | | |
|---|---|---|---|
| 5,482,925 A | 1/1996 | Hutsell | |
| 5,536,242 A * | 7/1996 | Willard | A61M 1/77 604/35 |
| 5,650,447 A | 7/1997 | Keefer et al. | |
| 5,665,085 A | 9/1997 | Nardella | |
| 5,758,663 A * | 6/1998 | Wilk | A61B 1/05 606/1 |
| 5,766,164 A * | 6/1998 | Mueller | A61B 18/22 606/17 |
| 5,827,216 A * | 10/1998 | Igo | A61M 1/77 604/176 |
| 5,893,848 A * | 4/1999 | Negus | A61B 18/1492 606/1 |
| 5,931,810 A | 8/1999 | Grabek | |
| 5,972,013 A | 10/1999 | Schmidt | |
| 6,092,526 A * | 7/2000 | LaFontaine | A61F 2/2493 128/898 |
| 6,156,009 A | 12/2000 | Grabek | |
| 6,161,543 A | 12/2000 | Cox et al. | |
| 6,206,004 B1 | 3/2001 | Schmidt et al. | |
| 6,231,518 B1 * | 5/2001 | Grabek | A61B 90/36 600/508 |
| 6,314,963 B1 | 11/2001 | Vaska et al. | |
| 6,569,082 B1 | 5/2003 | Chin | |
| 6,592,552 B1 | 7/2003 | Schmidt | |
| 6,695,769 B2 | 2/2004 | French et al. | |
| 6,709,382 B1 * | 3/2004 | Horner | A61M 60/497 600/16 |
| 6,780,178 B2 * | 8/2004 | Palanker | A61B 18/14 606/41 |
| 6,786,906 B1 | 9/2004 | Cobb | |
| 6,889,077 B2 * | 5/2005 | Bornzin | A61N 1/3987 607/63 |
| 6,918,890 B2 * | 7/2005 | Schmidt | A61B 17/3478 604/176 |
| 7,060,023 B2 | 6/2006 | French et al. | |
| 8,086,324 B1 * | 12/2011 | Vase | A61N 1/059 607/125 |
| 8,709,007 B2 | 4/2014 | Vaska | |
| 2003/0093104 A1 | 5/2003 | Bonner et al. | |
| 2005/0020901 A1 * | 1/2005 | Belson | G02B 23/2476 600/407 |
| 2005/0261673 A1 * | 11/2005 | Bonner | A61M 1/84 606/41 |
| 2005/0273129 A1 * | 12/2005 | Michels | A61B 17/3415 606/185 |
| 2020/0352647 A1 * | 11/2020 | Davies | A61B 18/1492 |
| 2023/0228755 A1 * | 7/2023 | Davidovits | G01N 33/5091 435/7.1 |

OTHER PUBLICATIONS

Miguel Valderrabano, David A. Cesario, Sen Ji, Kevin Shannon, Isaac Wiener, Charles D. Swerdlow, Hakan Oral, et al., "Percutaneous epicardial mapping during ablation of difficult accessory pathways as an alternative to cardiac surgery", Sep. 2004, pp. 311-316, vol. 1, No. 3, Publisher: Heart Rhythm Society, Published in: US.

\* cited by examiner

ELECTROSURGICAL PERICARDIAL PUNCTURE

CROSS-REFERENCES TO RELATED APPLICATIONS

This present application is a continuation-in-part of U.S. application Ser. No. 16/124,684, filed Sep. 7, 2018, issued as U.S. Pat. No. 11,298,184, which is a continuation of U.S. application Ser. No. 14/933,356, filed Nov. 5, 2015, issued as U.S. Pat. No. 10,166,070, which is a continuation-in-part of U.S. application Ser. No. 14/257,053, filed Apr. 21, 2014, issued as U.S. Pat. No. 9,179,932 which is a continuation-in-part of U.S. application Ser. No. 13/656,173, filed Oct. 19, 2012, issued as U.S. Pat. No. 8,702,692 which is a continuation-in-part of U.S. application Ser. No. 12/005,316, filed Dec. 27, 2007, issued as U.S. Pat. No. 8,308,720, which claims the benefit of U.S. provisional patent application 60/883,074, filed on Jan. 2, 2007. All of the aforementioned applications and patents are hereby incorporated by reference in their entirety.

TECHNICAL FIELD

The present invention relates to methods for treating the heart of a patient. More specifically, the present invention relates to methods of accessing the pericardial cavity of a patient's heart.

BACKGROUND OF THE ART

The pericardium is the outermost layer of the heart, surrounding the myocardium. The pericardium consists of two layers: an outer fibrous layer, and an inner serous layer. The inner serous layer is further sub-divided into two layers: an outer parietal layer, and an inner visceral layer. The inner visceral layer is referred to as the epicardium, and immediately covers the myocardium and the great vessels of the heart. Situated between the parietal layer and the epicardium is the pericardial cavity, a fluid-filled space typically containing approximately 20-25 mL of physiological fluid.

Certain cardiac conditions are treated by percutaneously inserting a needle through the outer layers of the pericardium into the pericardial cavity, and performing a treatment procedure from within the pericardial cavity. For example, ventricular tachycardia is often treated by inserting a needle into the pericardial cavity to provide access to the epicardium for catheter mapping and ablation procedures (Valderrabano et al. (2004), Heart Rhythm 1(3):311-6; Sosa et al. (2000) J Am Coll Cardiol 35:1442-9). This technique uses a standard epidural needle, which is inserted into the subxiphoid region, to puncture both the thoracic cavity and the outer layers of the pericardium. Once the needle has reached the pericardial cavity, catheter mapping and ablation procedures are performed on the epicardium.

This technique, however, has various risks associated with it, the most notable of which is the laceration of the myocardium by the needle. This risk is heightened in cases where the pericardial cavity and fluid volume is small. One report found accidental right ventricular laceration occurred in greater than 7% of patients (Sosa et al. (2000) J Am Coll Cardiol 35:1442-9).

The prior art includes alternative methods of accessing the pericardial cavity, but the methods described are relatively invasive and carry further risks to the patient.

SUMMARY OF THE DISCLOSURE

The problem of accessing the pericardial cavity while reducing the risk of damaging the myocardium layer is solved by a method comprising the steps of: (a) advancing a puncture device towards a heart, the puncture device including an energy delivery device at a distal end of the puncture device; (b) delivering a single pulse of a pulsed energy through the energy delivery device to a parietal pericardium of the heart to create a void relatively close to the energy delivery device while maintaining the distal end of the puncture device in a substantially stationary position relative to the parietal pericardium; (c) advancing the puncture device a short distance into the void; (d) checking if the puncture device has accessed the pericardial cavity by measuring pressure on the distal end of the puncture device; and (e) repeating steps (b), (c), and (d), if necessary, until the energy delivery device is located at least partially within the pericardial cavity. As used herein, the parietal pericardium refers to the two outer layers of the pericardium, including both the fibrous pericardium 232 as well as the parietal layer 234 (see FIGS. 2A to 2F). In some embodiments, the distance the puncture device is advanced in step (c) corresponds with either the thickness of the pericardial cavity or the parietal pericardium.

In one broad aspect of the invention, embodiments of a method of accessing a pericardial cavity of a heart, comprise the steps of: (a) advancing a puncture device towards a heart, the puncture device including an energy delivery device at a distal end of the puncture device; (b) delivering a single pulse of a pulsed energy through the energy delivery device to a parietal pericardium of the heart to create a void relatively close to the energy delivery device while maintaining the distal end of the puncture device in a substantially stationary position relative to the parietal pericardium; (c) advancing the puncture device a short distance into the void; (d) checking if the puncture device has accessed the pericardial cavity by measuring pressure on the distal end of the puncture device; and (e) repeating steps (b), (c), and (d), if necessary, until the energy delivery device is located at least partially within the pericardial cavity.

In some embodiments of the first broad aspect, step (c) comprises advancing the puncture device a distance greater than 0 mm and less than 1 mm. In some other embodiments, step (c) comprises advancing the puncture device a distance of about 1 mm between each delivery of energy. In some other embodiments, step (c) comprises advancing the puncture device a distance greater than 0 mm and less than 0.4 mm. In some embodiments, step (c) comprises advancing the puncture device a distance of from about 0.4 mm to about 1 mm.

For some embodiments of the first broad aspect, step (d) comprises measuring pressure using a transducer at the distal end of the puncture device. For some other embodiments the puncture device includes a lumen and an aperture at the distal end of the puncture device wherein the lumen is in fluid communication with the aperture, and step (d) comprises measuring pressure using an external pressure monitoring device which is in fluid communication with the lumen.

In some embodiments of the first broad aspect, step (b) includes using monopolar energy delivery. In some embodiments, step (b) includes using bipolar energy delivery. In some embodiments, step (b) includes using pulsed optical energy. In some embodiments, step (b) includes using DC electrical energy.

For some embodiments of the first broad aspect, step (d) includes injecting a contrast fluid such that the contrast fluid can be seen surrounding a cardiac silhouette. For some embodiments of the first broad aspect, step (d) includes aspirating fluid.

Some embodiments further comprise visualizing a position of a cannula using medical imaging, the cannula defining a lumen for receiving the puncture device. Some such embodiments further comprising positioning the cannula adjacent to a surface of a fibrous pericardium, using medical imaging. Some embodiments further comprise positioning the energy delivery device at a distal end of the lumen of the cannula, prior to delivering energy.

Some embodiments of the first broad aspect further comprise plotting an electrocardiogram to confirm a position of the energy delivery device. Some embodiments further comprise identifying contact between the energy delivery device and a tissue of the heart using an electrical impedance.

DETAILED DESCRIPTION

Figure 1A:
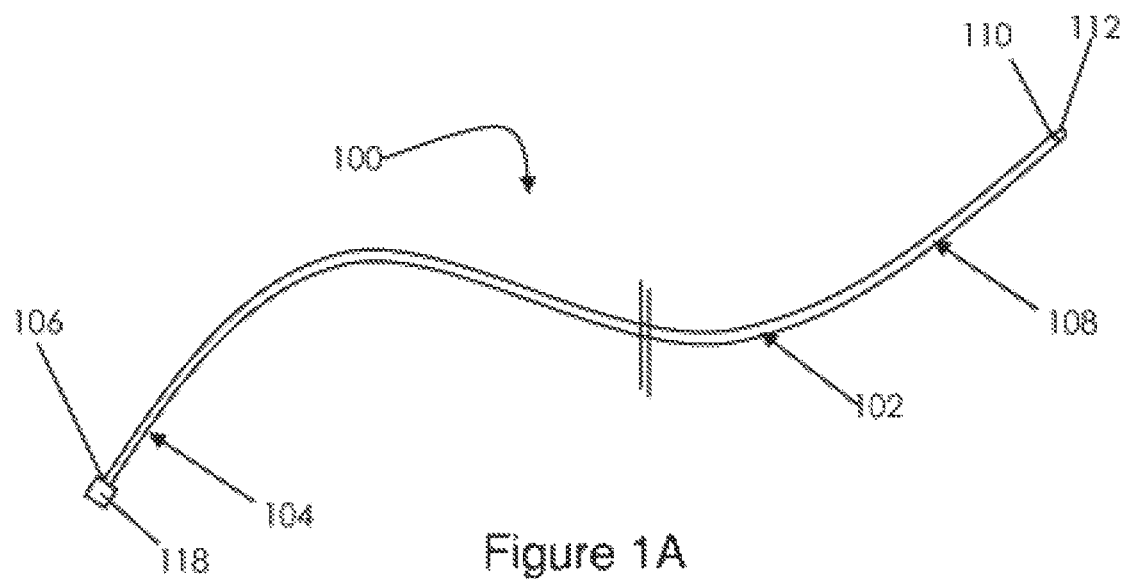
FIG. 1A is a perspective illustration of an embodiment of a puncture device that may be used in accordance with a method of the present invention.
Figure 1B:
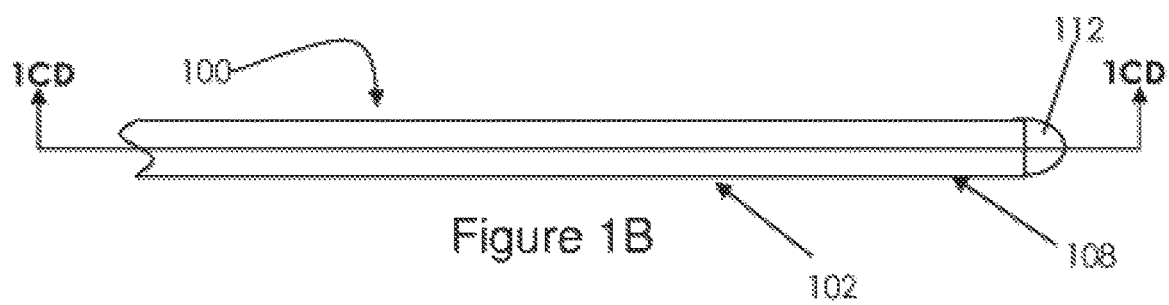
FIG. 1B is a partial plan view of an embodiment of a puncture device that may be used in accordance with a method of the present invention.

To gain access to the pericardial cavity for performing treatment procedures, such as catheter mapping and ablation, prior art devices typically comprise needles or other traumatic puncturing members that may cause damage to the myocardium when advanced towards the heart.

The present inventors have discovered a method which provides for safely accessing the pericardial cavity of the heart of a human or animal while minimizing the risk to the heart wall. Various embodiments of the method avoid the use of rigid piercing members and the associated risks.

The method includes advancing a puncture device towards the heart of a patient. The distal end of the puncture device is atraumatic and comprises an energy delivery device. The energy delivery device is positioned at a target site on a pericardium of the heart and energy is delivered from the energy delivery device to a tissue to create a channel to the pericardial cavity. The atraumatic distal end is blunt (not narrow and pointed like mechanical puncture needles are for being pushed through tissue), thereby facilitating using ultrasound for imaging the distal end of the puncture device. In contrast, the narrow pointed end of a typical mechanical needle is not sufficiently echogenic for effective ultrasound imaging. The atraumatic distal end also provides for improved safety over the use of narrow and pointed mechanical puncture needles (which can accidentally result in unintended damage to tissue). Typical embodiments of the method include using fluoroscopy for visualization. Some embodiments include using contrast fluid with the medical imaging.

One provided embodiment includes a method of accessing a pericardial cavity of a heart, the method comprising the steps of: (a) advancing a puncture device towards a heart, the puncture device including an energy delivery device at a distal end of the puncture device; (b) delivering a single pulse of a pulsed energy through the energy delivery device to a parietal pericardium of the heart to create a void relatively close to the energy delivery device while maintaining the distal end of the puncture device in a substantially stationary position relative to the parietal pericardium; (c) advancing the puncture device a short distance into the void; (d) checking if the puncture device has accessed the pericardial cavity by measuring pressure on the distal end of the puncture device; and (e) repeating steps (b), (c), and (d), if necessary, until the energy delivery device is located at least partially within the pericardial cavity. Such an embodiment allows the parietal pericardium to be punctured while keeping the puncture device substantially stationary relative to at least a portion of the parietal pericardium and at a safe distance from the myocardium. As used herein, "substantially stationary . . . relative to" refers to maintaining a relative position or distance between two bodies so that one does not move relative to the other, such as between a puncture device and a portion of the pericardium to be punctured. For example, in embodiments where the puncture device tents a portion of the parietal pericardium, then "substantially stationary . . . relative to" would indicate that the relative positions of the puncture device and pericardial portion are maintained.

In some embodiments, the portion of the parietal pericardium is manipulated by advancing the puncture device so that it tents the parietal pericardium into the pericardial cavity. As used herein, the parietal pericardium refers to the two outer layers of the pericardium, including both the fibrous pericardium 232 as well as the parietal layer 234 (see FIGS. 2A to 2F).

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Theory

As used herein, 'perforation' or 'puncture' refers to a procedure in which energy is applied from a device to a tissue to create a perforation, void, or channel through the tissue. The energy may be electrical current in the radiofrequency or microwave range, or the energy may be in the form of ultrasonic vibration, for example.

In the case of electrical current, and without being limited to a particular theory of operation, it is believed that during a perforation procedure the current serves to rapidly increase tissue temperature to the extent that water in the intracellular fluid becomes converted to steam, inducing cell lysis as a result of elevated pressure within the cell. Furthermore, electrical breakdown may occur between the cell and the electrode, wherein the electric field induced by the alternating current exceeds the threshold dielectric strength of the medium located between the electrode and the cell, causing a dielectric breakdown. This in turn may lead to electrical arcing which results in rapid cellular heating and cellular rupture. In addition, mechanical breakdown may occur, wherein an alternating current induces stresses on polar molecules in the cell, resulting in electroporation. Upon the occurrence of cell lysis and rupture, a void is created, allowing the device to advance into the tissue with little resistance. In order to achieve this effect, the device from which energy is applied, i.e. the electrode, must be relatively small, in order to increase the current density delivered to the tissue. In addition, the energy source must be capable of applying a high voltage, for example about 1600V Peak, through both a low impedance as well as a high impedance load, for example through about 300 ohms up to about 10000 ohms. Further details regarding the theory of radiofrequency perforation and systems suitable for radio-frequency perforation are found in U.S. patent application Ser. No. 11/265,304, filed on Nov. 3, 2005, issued as U.S. Pat. No. 7,947,040, and in U.S. patent application Ser. No. 11/520,754, filed on Sep. 14, 2006, issued as U.S. Pat. No. 7,828,796, both of which are incorporated herein by reference.

In the case of ultrasonic vibration, it is believed that mechanical vibrations pulverize tissue by mechanical impact, creating a channel through the tissue. In addition to direct mechanical perforation, high frequency vibration can create vapour-filled micro-bubbles which then expand and implode producing cavitations and liquid jets that can break cellular molecular bonds and erode the tissue.

Device

An example of a suitable device for use with embodiments of a method of the present invention will presently be described. It is to be noted, however, that the devices described herein are meant to be illustrative only.

Referring to FIG. 1, embodiments of an exemplary puncture device 100 for creating a channel through a tissue comprise an elongate member 102 having a proximal region 104 ending in a proximal end 106, and a distal region 108 ending in a distal end 110. As used herein, the terms 'proximal' and 'distal' are defined with respect to the user. That is, the term 'proximal' refers to a part or portion closer to the user, and the term 'distal' refers to a part or portion further away from the user, when the device is in use. An energy delivery device 112 is disposed at distal end 110 for delivering energy to the tissue to create a channel therethrough. In some embodiments, the energy delivery device is an electrically conductive and exposed component for delivering electrical current, i.e. an electrode, while in some other embodiments, the energy delivery device is structured for delivering vibrational energy, for example. In some embodiments comprising an energy delivery device for delivering vibrational energy, the vibrational energy is produced by an ultrasonic transducer located outside the patient's body and the vibrational energy then transmitted to the tissue via a means for transmitting vibrations, for example a wire and, more specifically, a nitinol wire. In some alternative embodiments, the energy delivery device comprises an ultrasonic transducer disposed at distal end 110 of device 100.

Figure 1C:
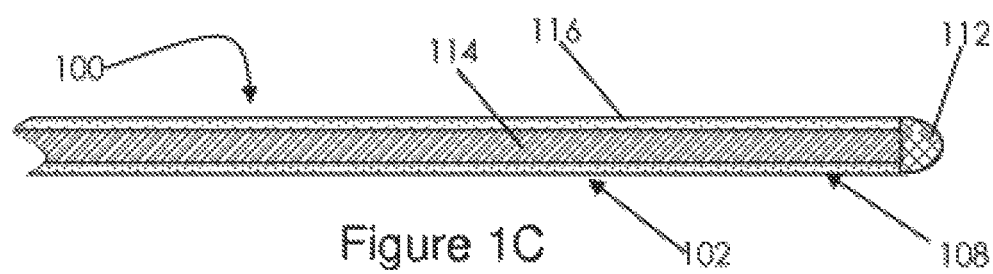
FIGS. 1C-1D are various embodiments of partial longitudinal cross-sectional views along the line 1CD-1CD in FIG. 1B.

In some embodiments, distal end 110 is substantially atraumatic to reduce the risk of accidental myocardial puncture and/or laceration. As shown in FIG. 1C, some embodiments of elongate member 102 comprise an electrically conductive wire 114 for operatively coupling energy delivery device 112 to a source of energy. Wire 114 is coated with an electrically insulative coating 116, which extends proximally from energy delivery device 112, as shown in FIG. 1C. Wire 114 may be coupled to energy delivery device 112 by welding, or soldering, for example. In the illustrated embodiment, proximal end 106 comprises a hub 118 for operatively coupling device 100 to an energy source.

Figure 1D:
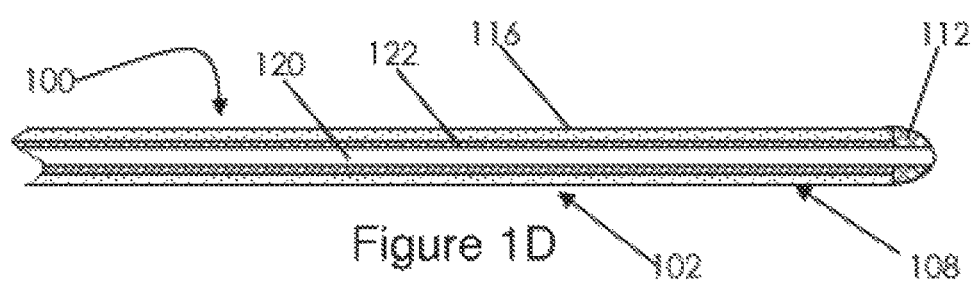

In some embodiments, device 100 defines a lumen 120 therethrough, as shown for example in FIG. 1D, such that material may be injected and/or withdrawn through distal end 110. In such embodiments, rather than a wire 114, elongate member comprises a hollow conductive tube 122. Alternatively, in some other embodiments, device 100 comprises a hollow insulated tube, for example a catheter, with a conductive wire embedded in a wall thereof.

Device 100 may further have various sensors associated therewith. For example, distal end 110 may comprise an impedance sensor, a temperature sensor, and/or a pressure sensor.

Figure 1E:
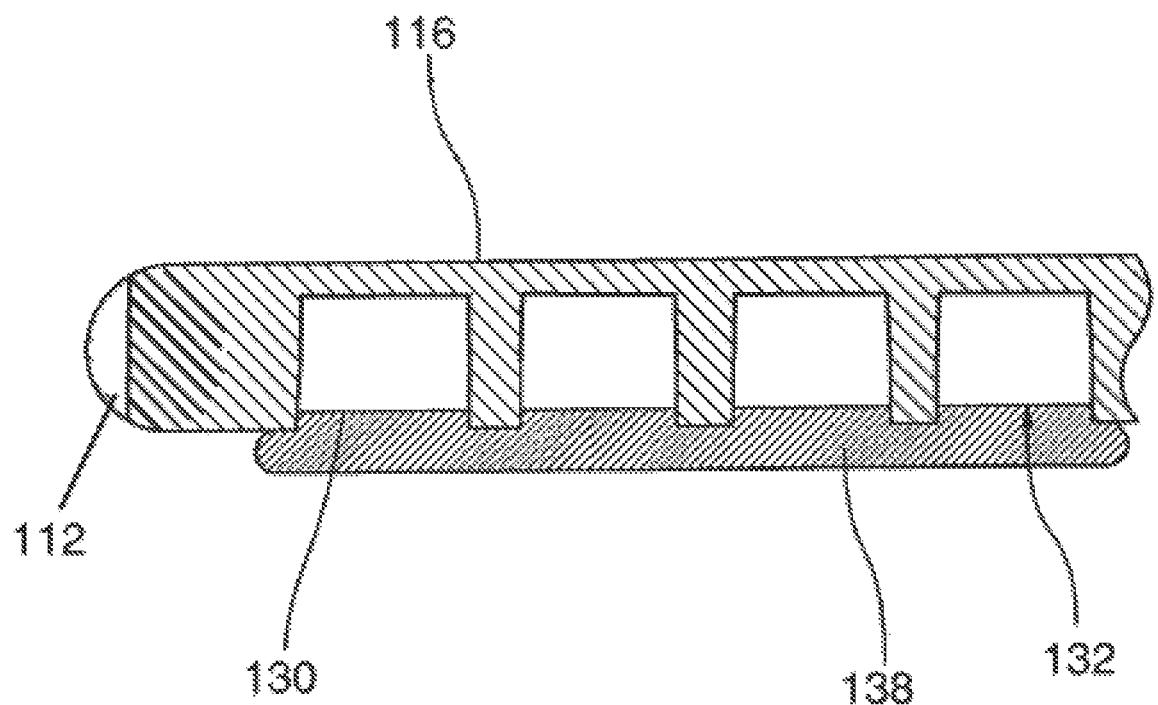
FIG. 1E is a side elevation view of an alternative embodiment of a puncture device that may be used in accordance with a method of the present invention.

In an alternative embodiment, a device used to perform a method of the present invention comprises a plurality of electrodes, for example at least one puncture electrode and at least one ablation electrode. An example of such an embodiment is illustrated in FIG. 1E, which shows a device including a puncture electrode (energy delivery device 112) located at a distal end of the device, as well as a plurality of ablation electrodes 130, which may also be referred to as "windows of conductivity" 132. As described herein above, puncture electrodes typically have a smaller surface area when compared to ablation electrodes, and may be used to create a channel through tissue by the delivery of high-frequency electrical energy. Ablation electrodes, on the other hand, are typically larger and typically used to create one of more lesions in a tissue. Such a device is particularly suitable for embodiments of a method of the present invention involving ablation of the epicardium 238, as will be described further herein below. Further details regarding similar devices are found in U.S. application Ser. No. 11/381,783, filed on May 5, 2006, incorporated herein by reference. In some embodiments, the same electrode is used for both perforation as well as ablation. For example, in some embodiments, the surface area of the electrode is altered during the course of the procedure to enable the electrode to create both a channel through tissue as well as a lesion. Alternatively, or in addition, the parameters of energy delivery may be altered such that both perforation and ablation are effected by a single electrode.

Further examples of suitable devices for creating a channel through a tissue by the delivery of energy include the PowerWire™ Radiofrequency (RF) Guidewire of Baylis Medical Company Inc. (Montreal, Canada), the Toronto Trans-septal Catheter of Baylis Medical Company Inc. (Montreal, Canada), as well as the Radiofrequency Puncture device described in U.S. Provisional Patent Application 60/827,452 (filed on Sep. 29, 2006) and the apparatus described in U.S. patent application Ser. No. 11/905,447, filed on Oct. 1, 2007, issued as U.S. Pat. No. 8,192,425, entitled "Radiofrequency Perforation Apparatus", incorporated herein by reference. An example of an energy source suitable for use with a puncture device is the Radiofrequency Puncture Generator of Baylis Medical Company Inc. (Montreal, Canada).

Methods

In one aspect, a method of the present invention comprises a method of accessing a pericardial cavity of a heart, the method comprising delivering electrical energy to a pericardium in a manner which creates a channel substantially through a parietal pericardium and does not substantially affect myocardial tissue.

An exemplary embodiment of this aspect comprises the steps of: delivering energy through an energy delivery device to an outer surface of a pericardium of a patient's heart, where the outer surface refers to the outermost layer of the pericardium; advancing the energy delivery device through the outer surface and through the parietal pericardium of the patient's heart; and stopping the delivery of energy when the energy delivery device has reached the pericardial cavity; whereby a channel is created from the outer surface of the pericardium to the pericardial cavity. Although the energy delivery device may be any device suitable for perforation as described above, an exemplary embodiment of the method will be presently described with reference to an active electrode as the energy delivery device used to create the perforation.

Prior to delivering energy to the pericardium, additional steps are performed in some embodiments. For example, various treatment compositions or medicaments, such as antibiotics or anaesthetics, may be administered to the patient, and various diagnostic tests, including imaging, may be performed.

Various approaches to insertion of an electrosurgical device may be required, depending on the particular procedure being performed. In one particular application of a method of the present invention, for example when treating epicardial arrhythmias such as ventricularParoxysmal supraventricular tachycardia (psvt)Ultrasound, ventricular septal defect-heartbeatVentricular assist deviceVentricular fibrillationVentricular septal defectVentricular tachycardia tachycardiaArrhythmiasMultifocal atrial tachycardiaParoxysmal supraventricular tachycardia (psvt)Sick sinus syndromeVentricular tachycardia, the patient is placed in the supine position, for example on an operating table, and the entry site on the patient's skin is cleaned and disinfected. In some embodiments, the entry site is located at the subxiphoid region of the patient's thorax.

In another application of a method of the present invention, for example when performing a pericardiocentesis procedure, the following approach is be used: the patient sits at 30-45° head elevation, which increases pooling of fluid toward the inferior and anterior surface, thus maximizing fluid drainage. In some such embodiments, the entry site is the subxiphoid region, on the left side.

In some embodiments, once the entry site has been determined, an introducer apparatus is used to puncture the thorax, for example, a cannula housing a removable obturator. The cannula is typically sized to house a puncture device such as the electrosurgical devices described hereinabove, as well as a sheath and/or dilator, as will be described hereinbelow. The obturator typically has a sharp distal end for piercing tissue. In some such embodiments, the introducer apparatus is inserted between the left border of the xiphoid process and the lower left rib, at an angle of approximately 45° towards the left scapula. In other embodiments, depending on the target location on the pericardium, the physician or user adjusts the orientation and positioning of the introducer as they see fit. For example, when performing a pericardiocentesis procedure, the needle is typically advanced toward the shoulder at an angle 15-20° from the abdominal wall.

When the distal tip of the introducer apparatus has penetrated the subcutaneous tissue, the user removes the obturator from the cannula. This aids in preventing damage to tissues and organs as the cannula is advanced through the thorax towards the heart. If the obturator is removed at this point of the procedure, a puncture device, for example as described hereinabove, may be inserted into the cannula. Alternatively, the puncture device may be inserted into the cannula later in the procedure.

In some embodiments, fluoroscopy is used to visualize the position of the cannula as it is advanced towards the heart. In one particular embodiment, the cannula is visualized from the left anterior oblique view at approximately 35-40°. Fluoroscopic visualization is typically enhanced by incorporation of a radiopaque marker on one or more of the cannula, the obturator and/or the puncture device. In some embodiments, the user injects a contrast solution through the cannula or through a lumen of the puncture device as they are being advanced towards the heart. In some embodiments, the cannula is advanced slowly towards the right ventricular apex of the heart (because it is mostly devoid of vessels).

Typically, the cannula is advanced until the distal end is substantially adjacent to the pericardium. Being adjacent to the tissue may include either being in contact with the tissue or close to the tissue without touching it. For example, using fluoroscopy, the cannula may be advanced within a few centimeters from the cardiac silhouette and then properly positioned for puncture of the pericardial sac. In addition to visualization, the user may discern when the cannula has reached the appropriate position by feeling a slight negative pressure due to the beating of the heart. That is, as the heart contracts, the user might feel a slight 'pulling' on the cannula. Alternatively, or in addition, fluoroscopy may reveal a V-shaped indentation (or "tenting") of the pericardium with contrast injection if the cannula is pressed against the pericardium.

FIGS. 2A-2F illustrate a portion of a patient's heart including a pericardium 226, a myocardium 228, and a ventricle 230. Pericardium 226 comprises a fibrous pericardium 232, a parietal layer 234, a pericardial cavity 236, and an epicardium 238.

Figure 2A:
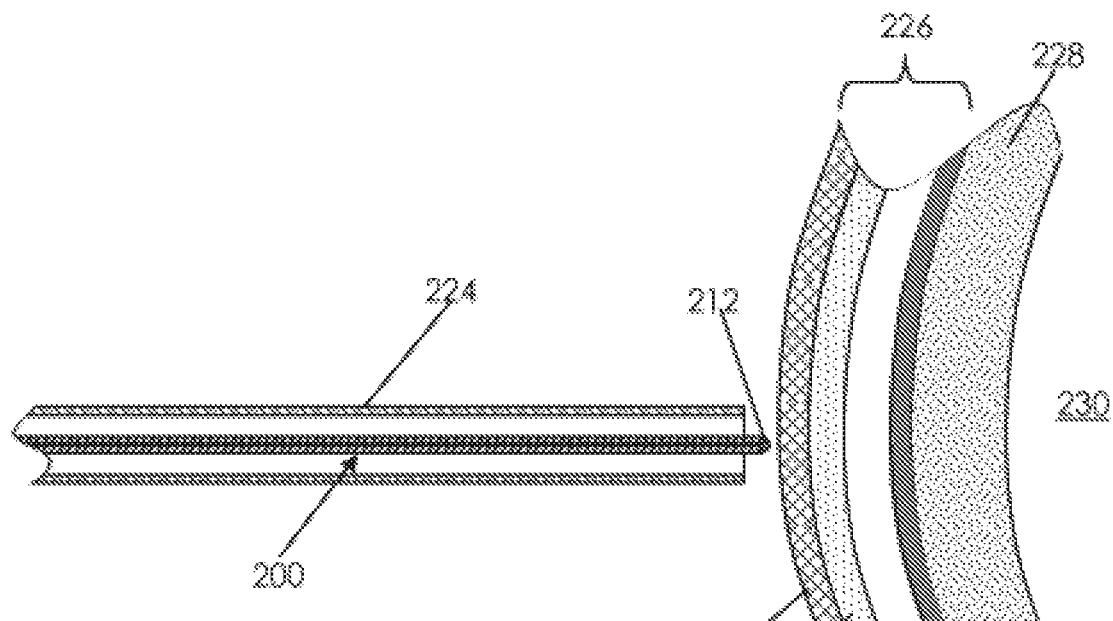
FIGS. 2A-2F are cross-sectional illustrations of the steps of one embodiment of a method of the present invention.

Referring to FIG. 2A, once the cannula 224 has reached the appropriate position proximate to the heart, the distal end of cannula 224 is positioned at the target site, which, in some embodiments, is on, at, or adjacent to the surface of the fibrous pericardium 232. Again, this might be facilitated by using fluoroscopic visualization or any other suitable medical imaging modality (for example, ultrasound, CT or MRI). The location of the target site may depend on numerous factors, including the nature of the procedure to be performed from within the pericardial cavity, and the specific anatomy of the patient's heart. For example, if the procedure to be performed is ablation of an epicardial re-entry site, the target site might be the portion of the pericardium above the medial third of the right ventricle. Alternatively, if the procedure to be performed is pericardiocentesis, the target site might be near the apex of the heart.

Once the distal end of cannula 224 has been positioned at the target site, the puncture device 200 may be inserted into cannula 224, if this was not previously done. Puncture device 200 may be any device from which energy is applied to create a perforation, void, or channel through the tissue, including, but not limited to, electrosurgical device 100 of FIG. 1. In some embodiments, puncture device 200 is inserted and positioned such that the energy delivery device 212 is located at the distal end of cannula 224, for example in contact with the outer surface of the pericardium at the target site. In some embodiments, the patient is asked to hold their breath, for example in order to limit respiratory movement.

Prior to the delivery of energy, a dispersive return electrode may be operatively coupled to the patient's body. In some embodiments, the dispersive return electrode comprises a grounding pad, which is placed on the skin of the patient. In alternative embodiments, the puncture device is operable in a bipolar manner, in which case a dispersive electrode is not required. A bipolar device may be further beneficial in that the energy delivered via the puncture device would remain concentrated around the two electrodes, substantially limiting the undesirable flow of current through structures such as the heart. Alternatively, if the energy delivery device comprises an ultrasonic transducer, a dispersive electrode would similarly not be required.

Figure 2B:
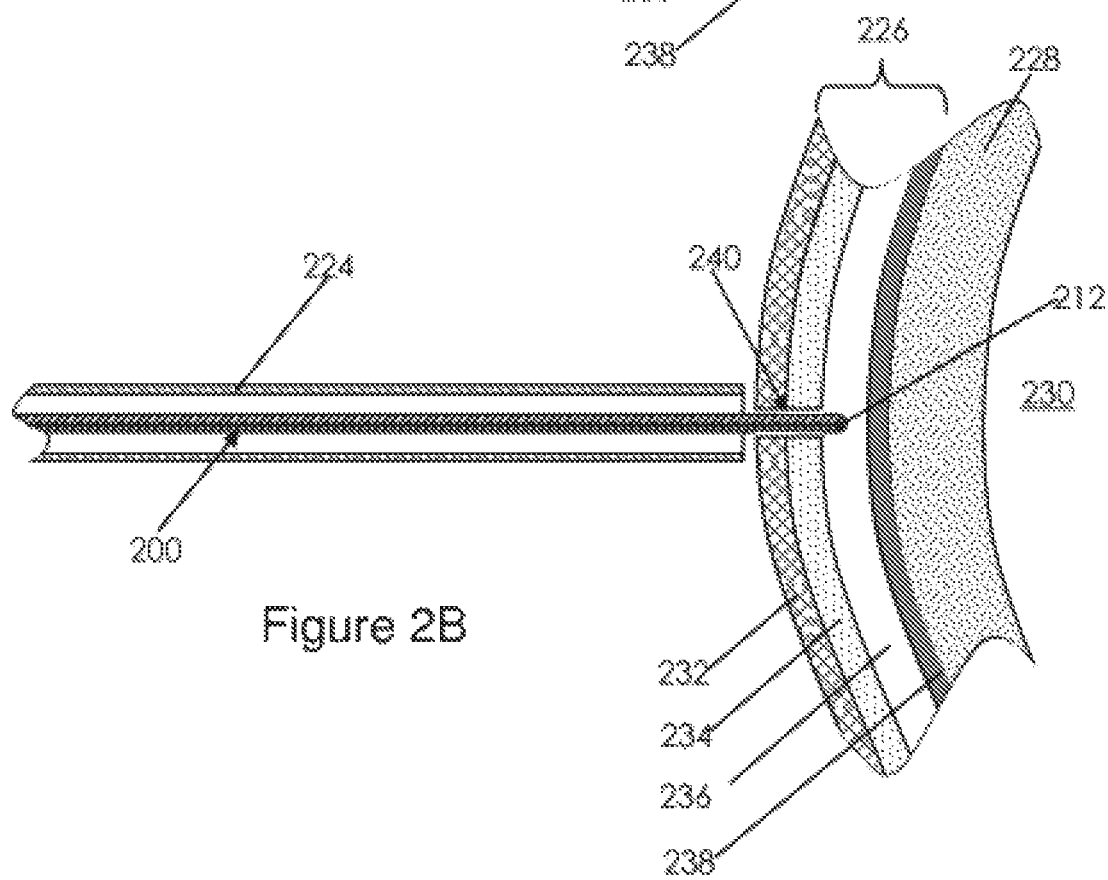

Referring now to FIG. 2B, a channel 240 is created through the outer layers 232, 234 of the pericardium by delivering energy from an energy source, such as a generator as described hereinabove, through energy delivery device 212 of puncture device 200, to the tissue of the pericardium. In some embodiments, wherein energy delivery device 212 comprises an active electrode, the energy delivered may be radiofrequency energy in the form of a sine wave, and may be at a voltage of between about 70V and about 1000V peak. In some embodiments, the user applies forward force to puncture device 200 as energy is being delivered, such that puncture device 200 advances through the tissue as channel 240 is created.

More particularly, the following procedure may be performed in order to create channel 240 through the outer layers 232, 234 of the pericardium. Slight forward pressure may be applied until the user, using tactile feedback, feels the heart pressing against the puncture device. The device is then pulled back slightly until the heart is no longer felt, at which point radiofrequency energy, for example, is delivered to create channel 240. Alternatively, as described hereinabove, the puncture device may be advanced until slight 'tenting' of the pericardium is visible under fluoroscopy without reaching the epicardium, at which point the electrical energy is delivered.

Following the delivery of energy, the position of the puncture device is typically confirmed and, if the channel 240 has been created substantially through to the pericardial cavity, the puncture device may be advanced slightly, taking care not to press against the epicardium (using, for example, tactile feedback or an electrocardiogram (ECG) to indicate when the puncture device is contacting the epicardium, where the ECG typically shows an injury response if the heart is contacted), and the delivery of energy may be repeated.

In alternative embodiments, rather than advancing puncture device 200 while delivering energy, the user positions energy delivery device 212 and times the delivery of energy such that the beating motion of the heart forces the pericardium against puncture device 200, thereby causing puncture device 200 to advance into the pericardium. For example, the user delivers energy during diastole, such that the heart expands towards the device, rather than physically advancing the device through the pericardium.

More specifically, in some such embodiments, the user delivers energy in response to a signal indicative of a cardiac cycle of the heart, such as an electrogram or electrocardiogram. Such an approach may be particularly beneficial when the level of fluid within the pericardial cavity is relatively normal, such that the space between parietal pericardium and the epicardium is relatively small. For example, procedures involving epicardial ablation may benefit from such an approach. In some such embodiments, the delivery of energy may be timed to occur in response to a particular feature of the cardiac cycle, as measured by the ECG signal. Timing the delivery of energy in response to the ECG signal may also be referred to as triggering or gating off of the ECG signal.

Figure 3:
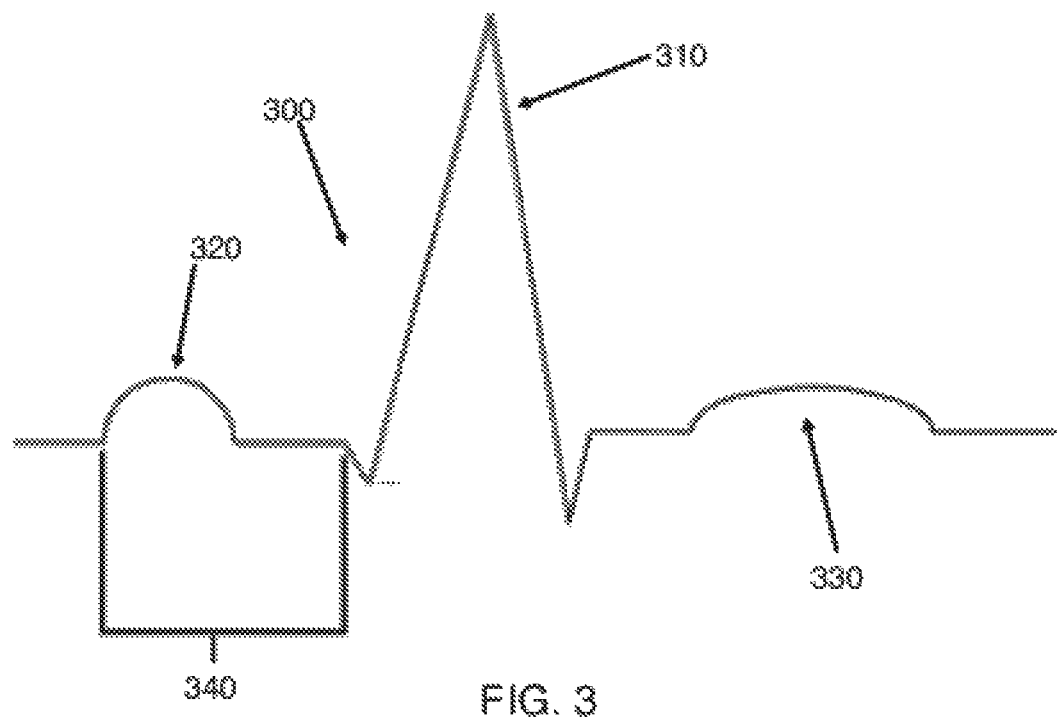
FIG. 3 is an illustration of a single cycle of a typical electrocardiogram (ECG) signal.

FIG. 3 is an illustration of a single cycle of a typical ECG signal 300. Typically, the feature of the ECG signal that is used for triggering is the QRS complex 310, as it generally has the highest amplitude. In some embodiments, the perforation energy should be delivered when the portion of the myocardium nearest the target site on the outer surface of the pericardium is furthest away from the puncture device, thereby reducing the risk of damaging or otherwise adversely affecting the myocardial tissue. For example, if the procedure involves ablating a location on a ventricle, in some embodiments, energy is delivered at least partially concurrently with the ejection of blood from the ventricles, which is indicated by T-wave 330 on ECG signal 300. Alternatively, if an ablation site is located on an atrium, the energy may be delivered at least partially concurrently with the ejection of blood from the atria and the filling of the ventricles, which is indicated by P-wave 320 on ECG signal 300. The period of time between the P-wave 320 and the R-wave of the QRS complex 310 is indicated by reference number 340 on FIG. 3. In order to deliver energy at least partially concurrently with the P- or T-waves, a user may adjust a delay of the trigger signal off of the QRS complex such that it causes energy to be delivered at the appropriate time. This delay would depend on the particular cardiac cycle of the patient being treated.

Figure 4:
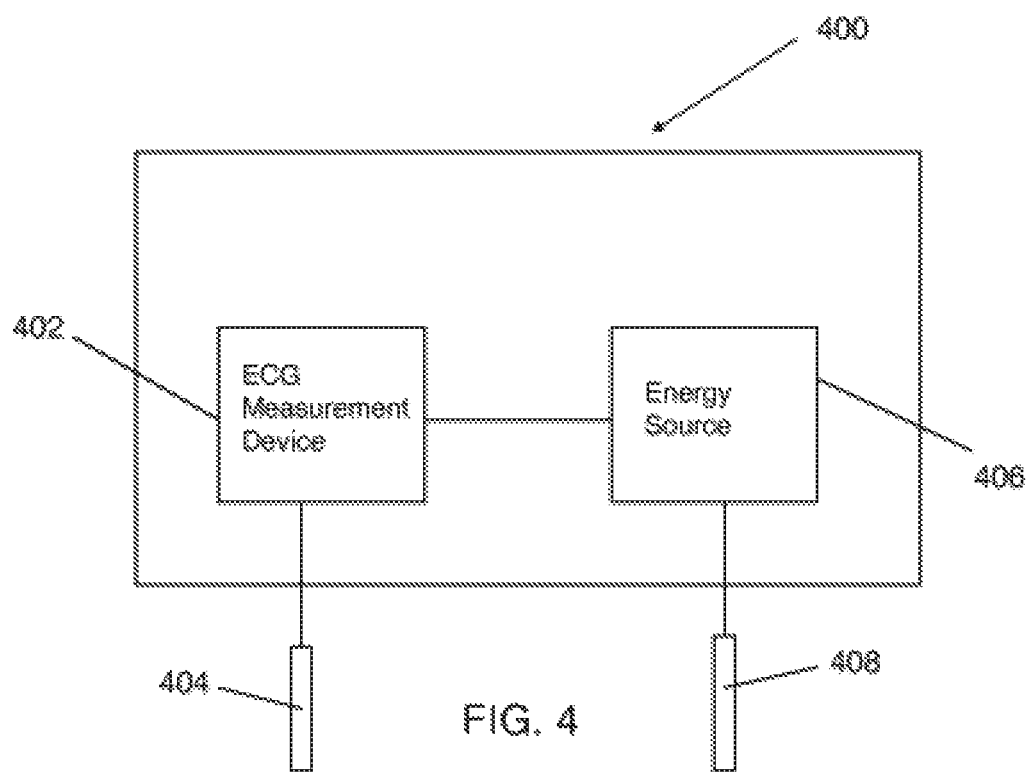
FIG. 4 is a block diagram illustrating an embodiment of a system that may be utilized in the present invention.

In some embodiments, the energy source used to generate the energy used for perforation is operable to communicate with an ECG measurement device, in order to deliver energy automatically in response to the ECG signal, thus obviating the need for user intervention. FIG. 4 shows an illustration of a system 400 incorporating both an ECG measurement device 402 as well as an energy source 406. In some embodiments, system 400 is a single unit, while in other embodiments ECG measurement device 402 and energy source 406 are housed in separate units but are operable to communicate with each other. In some embodiments, the communication is bi-directional, while in other embodiments the communication is uni-directional, with energy source 406 receiving trigger signals from ECG measurement device 402, and delivering energy accordingly. FIG. 4 further illustrates an ECG sensor 404 for delivering an ECG signal to ECG measurement device 402. In some embodiments, ECG sensor 404 comprises a plurality of ECG electrodes positioned on the body of a patient for measuring an ECG signal. In alternative embodiments, an ECG mapping catheter is positioned within the heart to measure the ECG signal. In addition, FIG. 4 illustrates a puncture device 408 for receiving perforation energy from energy source 406, as described hereinabove.

In some embodiments, the electrical energy is delivered in relatively short pulses of energy. The short duration of energy delivery adds a measure of safety and helps to ensure that the myocardium will not be substantially affected by the energy delivered to create channel 240 through the parietal pericardium.

Figure 6:
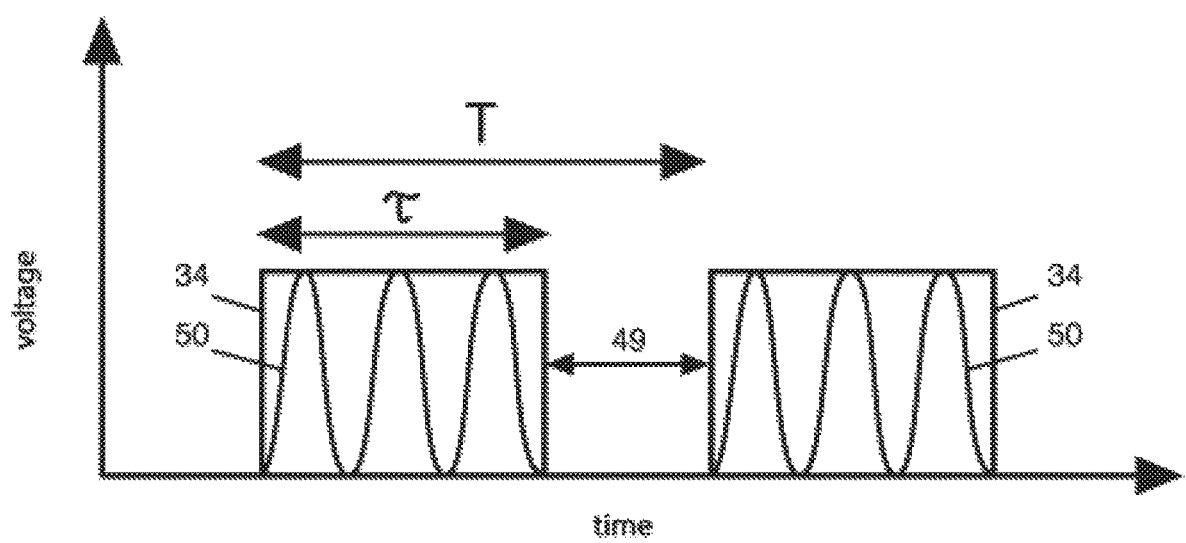
FIG. 6 is a graph of the energy delivery signal as may be delivered in an embodiment of the present invention.

FIG. 6 is a graph showing the amplitude and frequency of an energy delivery signal for an embodiment using monopolar delivery of pulsed energy. A pulse controller modulates the applied voltage resulting in pulses 34. Each pulse 34 is comprised of sinusoidal signal 50. The application of sinusoidal signal 50 over the time period τ of pulse 34 effectively acts as one pulse. Pulses 34 are separated by interval 49, with interval 49 and pulse time period τ adding up to a function period T. The function period T may also be described as the time of one control function cycle, for example, the time from the start of one pulse to the start of the next pulse, as is shown by line T in FIG. 6. While FIG. 6 illustrates only two pulses 34, as many pulses as are necessary are typically delivered in a procedure.

The time period τ of a pulse may range from about 5 ms (milliseconds) to about 1 second. Examples of the pulse time period τ of some embodiments are 5 ms, 25 ms, 100 ms, 300 ms or 1 second. The frequency of sinusoidal signal 50 may range from 100 kHz to 1000 kHz, and in a specific embodiment is about 460 kHz. In some embodiments, the power level ranges from about 2 W (watts) to about 25 W. In other embodiments, the power level ranges from about 25 W to about 100 W. In some embodiments, the peak voltage is greater than 250 $V_{peak}$. In some specific embodiments, the peak voltage ranges from about 250 $V_{peak}$ to about 2500 $V_{peak}$, and in some more specific embodiments, the peak voltage ranges from about 250 $V_{peak}$ to about 1000 $V_{peak}$. The embodiments having higher voltages may provide for safety by using shorter pulse periods than lower voltage embodiments. Some embodiments add a measure of safety by delivering energy at voltages that are sufficient to create arcing for puncturing but are not significantly above such levels. For example, some embodiments use a voltage of about 150 V RMS to about 250 V RMS, and some specific embodiments uses use a voltage of about 200 V RMS to create arcing.

The duty cycle of a pulse, i.e. the amount of time over which the pulse is "on" relative to the "off" time, may be defined as duty cycle D=τ/T (pulse time period τ divided by function period T). In some embodiments of the method, the pulsed energy has a duty cycle D of at least about 0.1%, in more specific embodiments the duty cycle D is at least about 0.5%, and in yet more specific embodiments the duty cycle D is at least about 5%. In typical embodiments, the duty cycle is selectable.

In embodiments including delivery of pulsed energy, a selected quantity of pulses may be delivered. In some such embodiments, the selected quantity of pulsed energy is a single pulse, while in other embodiments the selected quantity of pulsed energy is more than one pulse.

Some pulsed energy embodiments provide further safety enhancements, including delivering energy when puncture device 200 is substantially stationary relative to the tissue to which energy is being delivered and advancing the puncture device 200 between energy deliveries rather than advancing while delivering energy. The method comprises delivering pulsed energy through energy delivery device 212 of puncture device 200 to the parietal pericardium while maintaining the distal end of the puncture device in a substantially stationary position relative to the parietal pericardium. Each delivery of energy creates a void relatively close to the electrode of energy delivery device 212. When a selected period of energy delivery is completed, puncture device 200 can then be advanced. Typically, the steps of delivering energy for a short period of time and advancing a short distance into the void created by an energy delivery are repeated a number of times. In some cases, the remaining wall of the parietal pericardium is sufficiently thin enough that during the step of mechanical advancement, puncture device 200 will puncture through the parietal pericardium wall and enter pericardial cavity 236. In other cases, a final delivery of energy will provide a channel for entering pericardial cavity 236.

Delivery of energy in brief pulses further enhances the safety of the procedure, since the pulsed energy is delivered relatively close to the electrode and the pericardial cavity 236 provides a fluid filled gap of between 1 and 2 millimeters (mm) between the parietal pericardium and the endocardium, thereby reducing the risk of damage to the endocardium due to the energy delivery. Considering the above dimensions of the pericardial cavity 236, some embodiments of the above method of delivering a single pulse 34 of energy include advancing the puncture device 200 a distance greater than 0 mm and less than 1 mm. Other embodiments advance the puncture device a distance of about 1 mm between each delivery of energy.

As puncture device 200 is advanced, the physician receives tactile feedback. If the distal end of puncture device 200 has entered pericardial cavity 236, the physician may feel a release of tension in the puncture device. The physician may also confirm that puncture device 200 has entered pericardial cavity 236 using others means described herein. In a specific embodiment, the physician attempts to advances puncture device 200 between each delivery of a single pulse of energy, and, optionally, checks to ascertain whether or not puncture device 200 has entered pericardial cavity 236 between the pulses. In some embodiments, a generator is programmed to deliver pulses of energy at a pre-determined interval, allowing sufficient times between pulses for the physician to attempt to advance the puncture device and, optionally, perform any other test to ascertain whether or not puncture device 200 has entered the pericardial cavity 236. In alternative embodiments, a user interacts with the generator to deliver the pulses of energy.

In alternative pulsed energy embodiments, the puncture device 200 is operable in a bipolar manner, in which case a dispersive electrode is not required. Alternatively, if the energy delivery device comprises an ultrasonic transducer, a dispersive electrode would similarly not be required.

In some alternative embodiments, the method of using pulsed energy uses pulsed optical energy. In other alternative embodiments, the method comprises the delivery of DC electrical energy.

The user typically stops the delivery of energy when energy delivery device 212 has reached pericardial cavity 236, as shown in FIG. 2B. Stopping the delivery of energy when energy delivery device 212 has reached pericardial cavity 236 facilitates ensuring that myocardium 228 of the heart is not penetrated by puncture device 200, thus preventing unwanted damage to myocardium 228.

In one embodiment, in order to ascertain when energy delivery device 212 has reached pericardial cavity 236, the energy is delivered for a substantially brief duration, e.g. in pulses, as described hereinabove, with a time period between pulses when substantially no energy is delivered. During any one or more of these time periods when substantially no energy is delivered, the user injects contrast solution through the distal end of puncture device 200. A typical puncture device 200 has a port, such as a side port or aperture (not shown), for delivering the contrast fluid. If the distal end of puncture device 200 has not reached pericardial cavity 236, the contrast solution will accumulate in the mediastinum. If the distal end of puncture device 200 is located within pericardial cavity 236, the contrast solution will be seen surrounding the cardiac silhouette, thus providing an indication to the user that the pericardial cavity has been reached. In alternative embodiments, the step of checking for or confirming access to the pericardial cavity 236 comprises confirming the location of the distal end of the puncture device 200 by measuring electrical impedance at the distal end of the device 200.

Anatomical cadaver studies have reported a typical pericardial thickness of 0.4 to 1 mm (millimeter). As such, the time for a puncture to occur will vary depending on the pericardial thickness of the patient being treated. Furthermore, puncture time varies depending upon the voltage applied to the tissue.

Considering the above pericardial (parietal pericardium) thickness dimensions, some embodiments of the above method of delivering a single pulse 34 of energy include advancing the puncture device 200 a distance greater than 0 mm and less than 0.4 mm. Other embodiments advance the puncture device a distance of from about 0.4 mm to about 1 mm between each delivery of energy.

When a channel has been created through the parietal pericardium, mechanical resistance to advancement of the puncture device 200 is reduced, which a physician may ascertain through tactile feedback. Once the channel providing access to the pericardial cavity is created, puncture device 200 might be advanced without energy delivery. In typical embodiments, the distal end portion of puncture device 200 is relatively flexible (in comparison to the proximal end portion) in order to facilitate advancing the device into the pericardial cavity 236 and, optionally, along the surface of the heart wall, while the proximal end portion of device 200 is relatively more rigid than the distal end portion in order to provide pushability (i.e. to allow transmission of pushing force). The flexibility of the puncture device 200 also reduces and/or prevents trauma to the myocardium and other heart layers. Once puncture device 200 has been advanced into pericardial cavity 236 it can be used to advance dilators, sheaths, and other medical devices into pericardial cavity 236 as explained hereinabove.

In an alternative embodiment, rather than injecting contrast, a user aspirates fluid between the periods of energy delivery. Upon reaching the pericardial cavity, pericardial fluid is aspirated, providing confirmation to the user that the pericardial cavity has been reached. In a further embodiment, a user measures pressure exerted on a distal end of the device, where the pressure exerted may be fluid pressure or pressure exerted by a tissue contacting the distal end of the device. Measuring pressure exerted on the distal end of the device thus serves to indicate if the distal end is located within the pericardial cavity and may also indicate whether or not the distal end is contacting the epicardium.

In any of the aforementioned embodiments, the means of confirmation, i.e. injection of contrast, aspiration of fluid or measurement of pressure, may be accomplished utilizing the same device that is used to deliver the perforation energy to the pericardium. For example, as described hereinabove, an electrosurgical device defining a lumen longitudinally therethrough may be used both for delivering energy as well as for injection of contrast, aspiration of fluid and/or measurement of fluid pressure exerted on the distal end of the electrosurgical device.

One means to measure a pressure at the distal end of the puncture device 200 includes a transducer at the tip of puncture device 200. Another means to measure pressure at the distal end of the puncture device 200 includes a continuous lumen 120 through the length of the puncture device 200 in fluid communication with a distal end aperture (e.g. FIG. 1D) and an external pressure monitoring device.

Another embodiment of the method of accessing the pericardial cavity 236 of a heart comprises the steps of: (a) advancing a puncture device 200 towards a heart, the puncture device 200 including an energy delivery device 212 at a distal end of the puncture device; (b) delivering a single pulse 34 of a pulsed energy through the energy delivery device 212 to a parietal pericardium of the heart to create a void relatively close to the energy delivery device 212 while maintaining the distal end of the puncture device 200 in a substantially stationary position relative to the parietal pericardium; (c) advancing the puncture device 200 a short distance into the void; (d) checking if the puncture device 200 has accessed the pericardial cavity 236 by measuring pressure on the distal end of the puncture device 200; and (e) repeating steps (b), (c), and (d), if necessary, until the energy delivery device 212 is located at least partially within the pericardial cavity 236.

In yet another embodiment, the user monitors the electrical impedance at energy delivery device 212 to ascertain when at least a portion of energy delivery device 212 has reached pericardial cavity 236. In other words, puncture device 200 comprises an impedance sensor, which in some embodiments comprises the energy delivery device itself, which measures the electrical impedance at energy delivery device 212. Due to the presence of fluid in pericardial cavity 236, the outer layers 232, 234, of the pericardium will have different impedances than that seen within pericardial cavity 236. For example, the impedance of the tissue of the outer layers of the pericardium may be greater than about 400 ohms, and the impedance of the pericardial fluid may be between about 100 and about 300 ohms. Thus, if the user monitors the impedance as device 200 is advanced, the user typically manually stops the delivery of energy when a change in impedance indicates that energy delivery device 212 is located at least partially within pericardial cavity 236. In a further embodiment, the energy source and puncture device 200 are operable such that the delivery of energy is automatically stopped when a change in impedance indicates that energy delivery device 212 is located at least partially within pericardial cavity 236.

Making further reference to FIGS. 2A and 2B, a method of the present invention for accessing a pericardial cavity 236 of a heart using impedance comprises: advancing a puncture device 200 towards the heart, the puncture device 200 including an energy delivery device 212; measuring an electrical impedance at the energy delivery device 212; delivering energy from the energy delivery device 212 to at least partially puncture a pericardium 226; and repeating one or more of the above steps, if necessary, until the energy delivery device 212 is located at least partially within the pericardial cavity 236. In some embodiments, delivering energy and advancing are performed at least partially concurrently, while in other embodiments, delivering energy and advancing are performed non-concurrently. The type of energy delivered can be electrical energy, ultrasonic energy, or any other suitable type of energy. Some embodiments include the step of measuring electrical impedance being performed using energy delivery device 212. In some examples of the method, the electrical impedance is measured while advancing puncture device 200. In some examples of the method, the electrical impedance is measured after advancing puncture device 200.

Some embodiments of the method of using impedance further comprise visualizing a position of a cannula 224 that is advanced towards the heart using medical imaging, wherein the cannula defines a lumen for receiving puncture device 200. Details regarding the advancement of cannula 224 are described hereinabove with regards to FIGS. 2A to 2F. Some such embodiments further comprise positioning cannula 224 adjacent to a surface of a fibrous pericardium 232 using medical imaging. In typical embodiments, medical imaging is performed in more than one plane. Some examples yet further comprise positioning energy delivery device 212 within a distal end of the lumen of the cannula, prior to delivering energy.

In some embodiments, the method further comprises measuring an electrocardiogram (ECG) to confirm the position of energy delivery device 212. In some such embodiments, ST elevation is typically measured around a ventricle.

Attempts have been made in the past to measure impedance or measure voltage to plot an ECG in various procedures using an uninsulated needle, often arriving at results with errors or inaccuracies. Typical embodiments of puncture device 200 comprise a layer of insulation that leaves energy delivery device 212 exposed wherein energy delivery device 212 defines an electrode at the distal end of puncture device 200. This allows for impedance or an ECG plot to be measured or determined at the location of energy delivery device 212. The inventors have discovered unexpectedly that improved impedance and ECG results can typically be obtained using a smaller electrode associated with an insulated needle, such as energy delivery device 212, than are obtained using a larger electrode defined by a bare uninsulated needle.

Some embodiments of the method of using impedance further comprise identifying if there is contact between energy delivery device 212 and a tissue of the heart using the measured electrical impedance and, optionally, determining what tissue is being contacted. For example, measured impedance typically has a strong T-wave if energy delivery device 212 is contacting a ventricle.

In some embodiments of the method of using impedance, the method further comprises tenting the pericardium of the heart. Some such embodiments further comprise visualizing the step of tenting using medical imaging, and may further comprise delivering a contrast fluid outside of, and optionally adjacent to, the pericardium. Some examples of tenting further include using tactile feedback to confirm tenting of the pericardium. Tenting is described hereinbelow in more detail with reference to FIG. 5.

Some embodiments of the method further comprise a step of stopping energy delivery when a change in the electrical impedance indicates that energy delivery device 212 is located at least partially within the pericardial cavity. For example, the impedance of the tissue of the outer layers of the pericardium is typically greater than about 400 ohms, and the impedance of the pericardial fluid is typically between about 100 and about 300 ohms. In one specific embodiment, the impedance external to the pericardial sac (i.e. outside of the pericardium) is found to be about 200 ohms and about 100 ohms within pericardial cavity 236. Some embodiments of the method further comprise stopping advancement of the puncture device 200 as a result of a change in impedance as described above.

Some embodiments of the method of using impedance further comprise using tactile feedback to ascertain when the energy delivery device 212 is located at least partially within a pericardial cavity 236.

In some embodiments of the method of using impedance, the method further comprises injecting a contrast fluid into pericardial cavity 236 to confirm that energy delivery device 212 is at least partially within the pericardial cavity. In some such embodiments, the step of injecting a contrast fluid is performed using puncture device 200. In some alternative embodiments, fluid is delivered through an introductory device or introducer apparatus such as cannula 224. Some embodiments of the method further comprise aspirating fluid from pericardial cavity 236 to confirm that energy delivery device 212 is at least partially within the pericardial cavity. In some such embodiments, the step of aspirating fluid is performed using puncture device 200.

Some embodiments of the method further comprise measuring voltage with a bipolar device (e.g. a device with an active electrode and a return electrode, for example on a single shaft or elongate member) to plot or measure a bipolar electrocardiogram to confirm that energy delivery device 212 is at least partially within pericardial cavity 236. Typically, impedance increases significantly when a bipolar energy delivery device 212 punctures a pericardium and enters the pericardial cavity. In some examples, the impedance increases from zero ("a flat line") when the energy delivery device has not yet touched the heart to a level readable or measurable by a user.

In another embodiment, as described hereinabove, the user uses tactile sensation to ascertain when at least a portion of energy delivery device 212 has reached pericardial cavity 236. In other words, when energy delivery device 212 has penetrated outer layers of the pericardium 232, 234, and has entered pericardial cavity 236, the mechanical resistance felt by the user changes, for example the user may feel less resistance, at which point the user typically stops the delivery of energy to avoid unwanted damage to the myocardium.

In a further embodiment, a user visualizes the location of the puncture device using an imaging device positioned in proximity to the puncture device. For example, in some such embodiments, an intracardiac echocardiographic (ICE) imaging catheter is positioned within the heart and is used to visualize the position of the puncture device. Alternatively, an imaging catheter may be positioned within the coronary sinus.

Figure 2C:
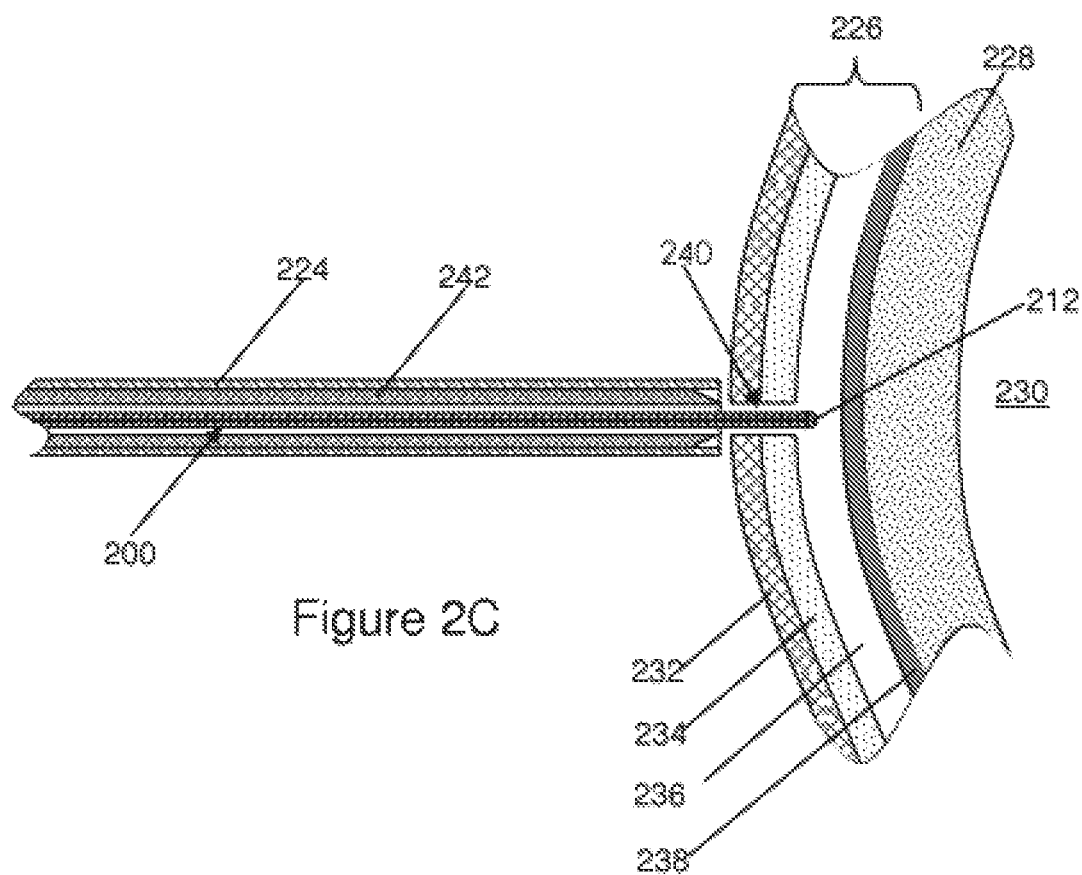
Figure 2D:
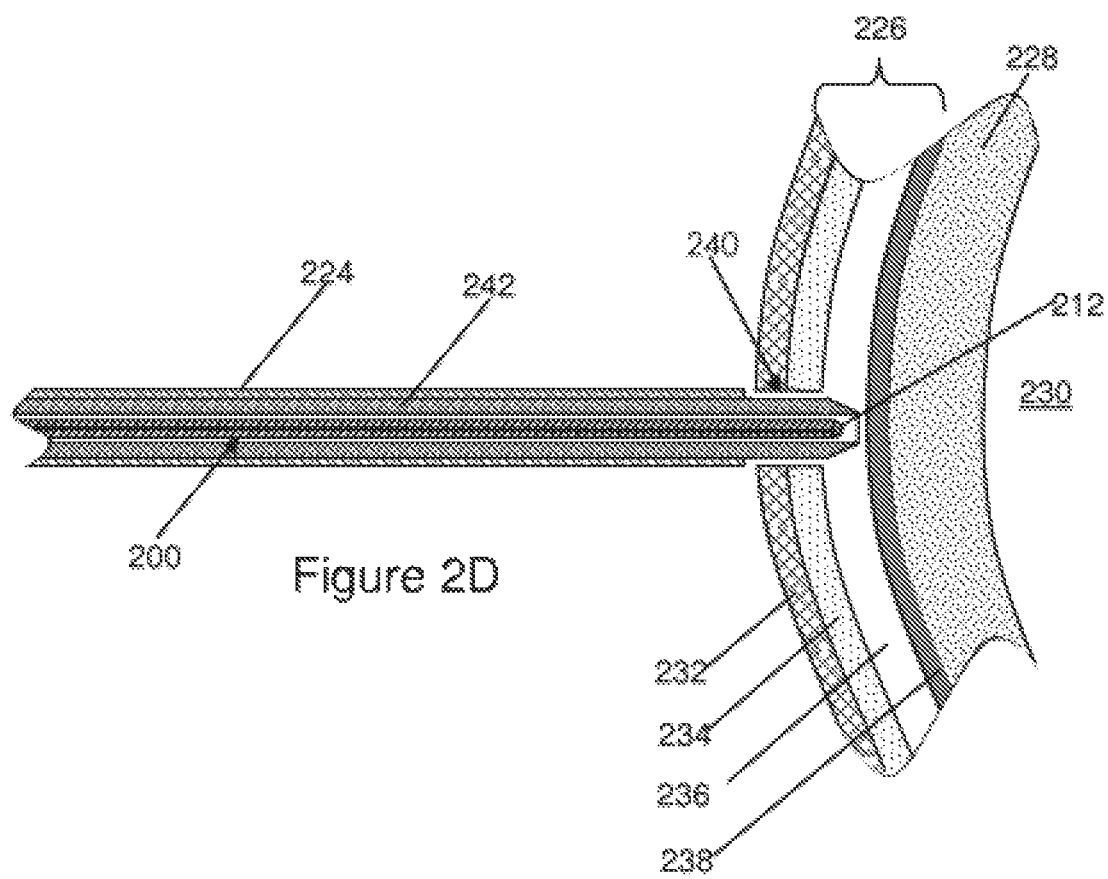

With the distal end of puncture device 200 positioned within pericardial cavity 236, the user may choose to dilate channel 240, and may position a sheath or cannula within channel 240 to maintain patency of channel 240. For example, in some embodiments, a dilator 242 is advanced through cannula 224, and over puncture device 200, as shown in FIG. 2C. The distal region of dilator 242 is advanced through channel 240, such that channel 240 is dilated, as shown in FIG. 2D. Dilator 242 typically has a substantially circular and blunt distal end in order to minimize the risk of accidental myocardial perforation. In addition, dilator 242, in some embodiments, is tapered, which allows for a more gradual dilation of channel 240 to help maintain hemodynamic stability.

Figure 2E:
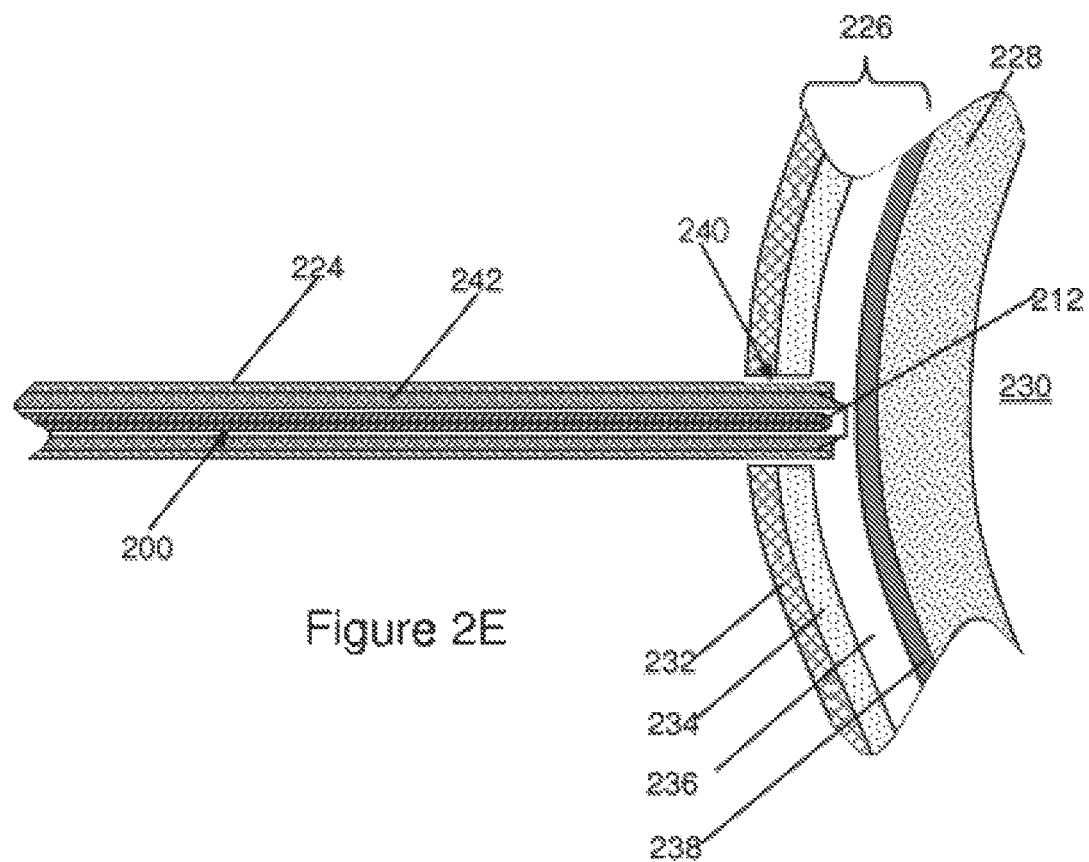
Figure 2F:
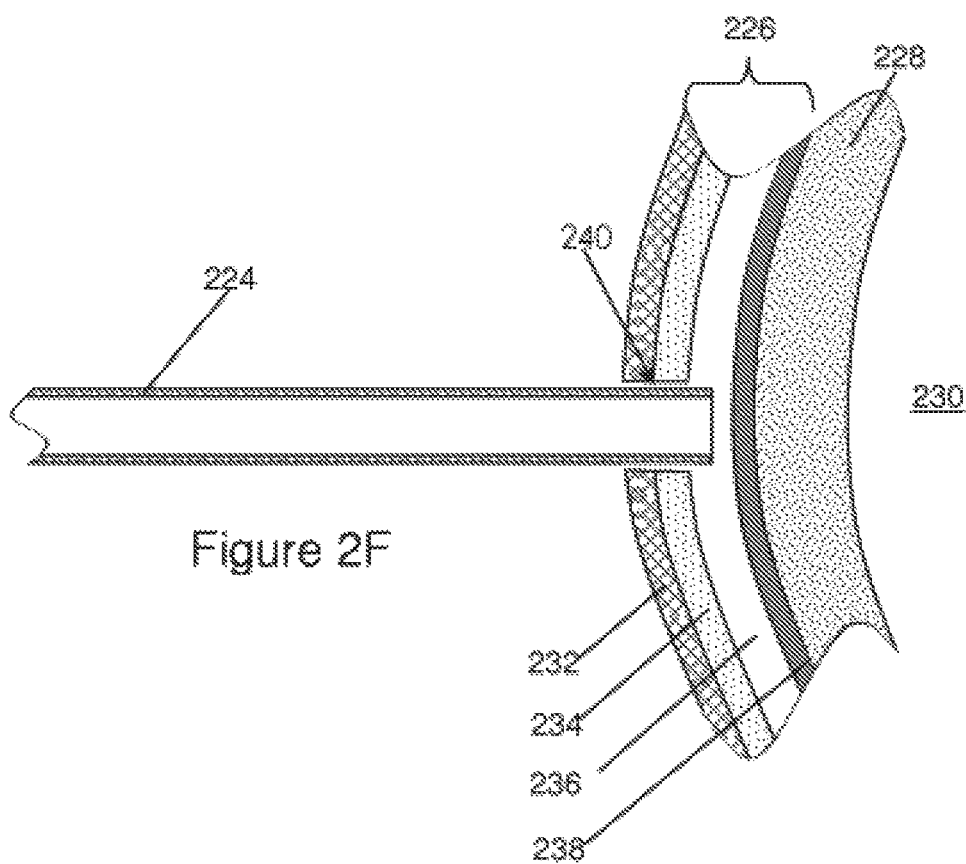

Referring now to FIG. 2E, the distal end of cannula 224 is then, in some embodiments, advanced over dilator 242, into pericardial cavity 236. Puncture device 200 and dilator 242 may then be withdrawn from pericardial cavity 236, if so desired by the user, and removed from the patient's body, leaving only cannula 224 in place in pericardial cavity 236, as shown in FIG. 2F. Cannula 224 is then operable to serve as a conduit for other surgical devices to access the pericardial cavity. In alternative embodiments, a sheath is advanced through cannula 224, over both puncture device 200 and dilator 242. The distal end of the sheath may be advanced into pericardial cavity 236 along with the distal end of the dilator. The sheath and dilator may be advanced substantially concurrently or at least partially sequentially. In some examples, the dilator 242, puncture device 200, and cannula 224 are then removed from the patient's body, leaving only the sheath in place in pericardial cavity 236. The sheath is then able to serve as a conduit for other surgical devices. For example, a guidewire may be introduced into the pericardial cavity, or a pericardiocentesis needle introduced through cannula 224 or the sheath in order to drain fluid from the pericardial cavity. Alternatively, in embodiments utilizing a separate ablation catheter for epicardial ablation, the ablation catheter is typically introduced through cannula 224 or the sheath, and an ablation procedure then performed on the myocardium.

In further embodiments, a method of the present invention is utilized for lead placement in biventricular pacing or for placing other devices that may be helpful for heart failure. Alternatively, embodiments of the method are used for infusing medications, for example antiarrhythmic agents, directly on the ventricle surface, or to inject growth factors or stem cells to stimulate blood vessel growth or tissue regeneration.

In an alternative embodiment, a method of the present invention comprises a first step of positioning the puncture device 200 adjacent to tissue of the parietal pericardium.

Figure 8A:
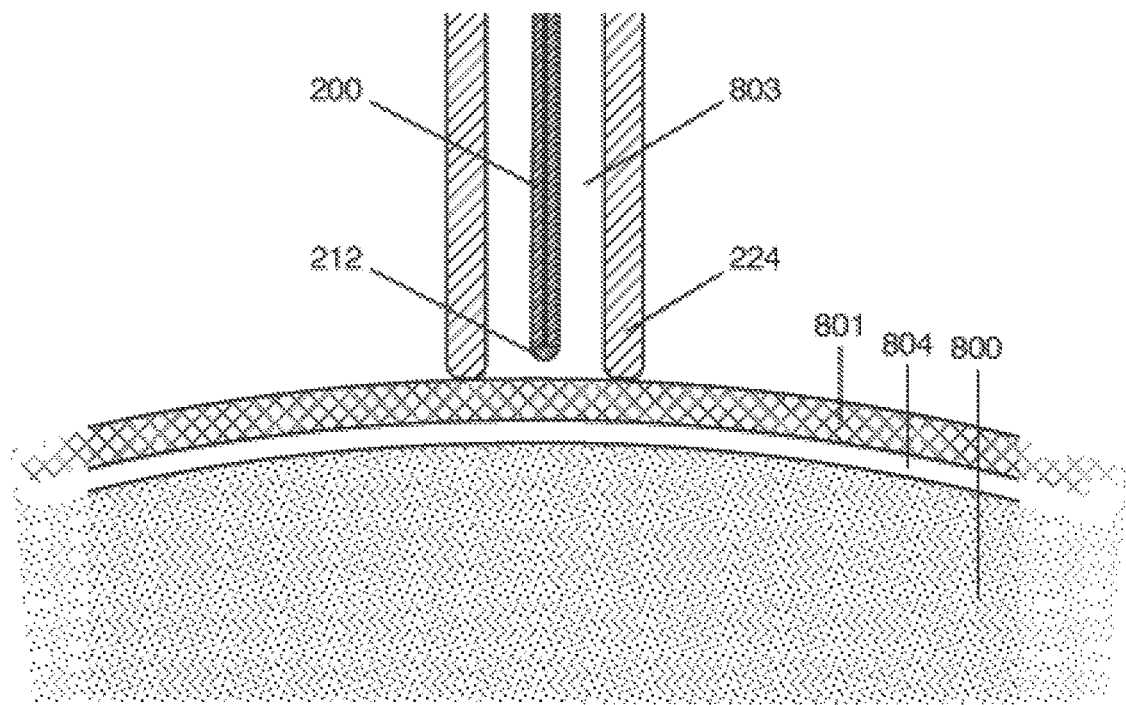
FIGS. 8A-8C are cross-sectional illustrations of the steps of an embodiment of a method of the present invention.
Figure 8B:
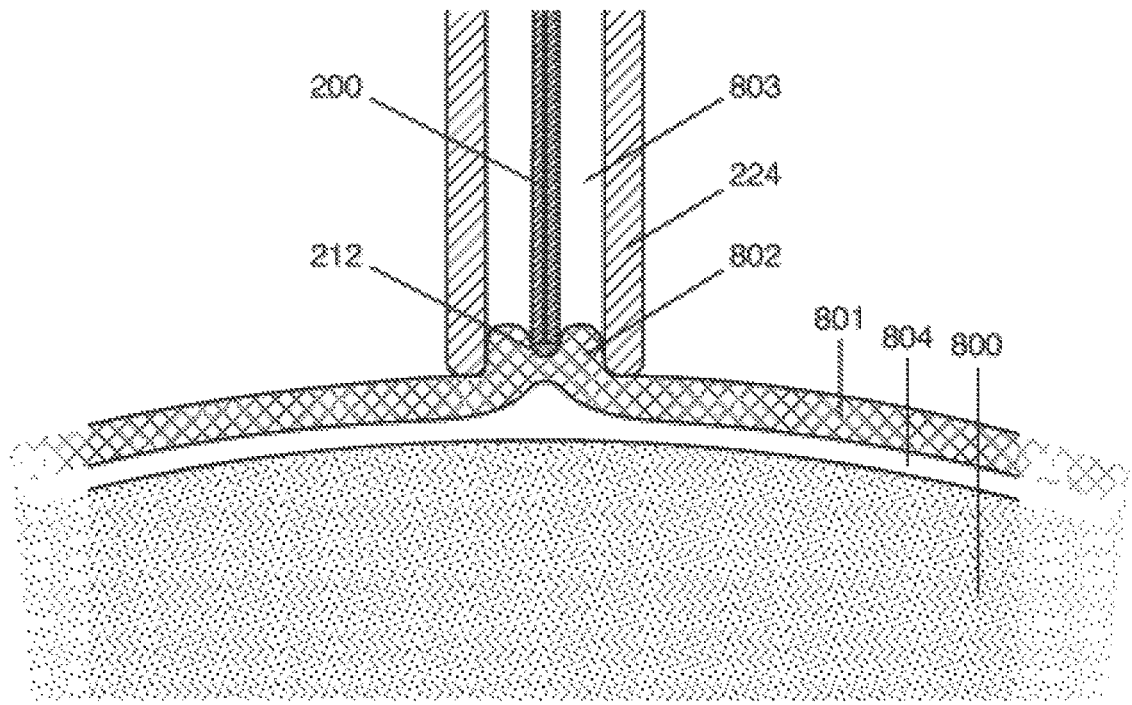

The second step of this alternative embodiment is manipulating a portion of the parietal pericardium so that the portion is in tension against the distal end of the puncture device 200. In some such embodiments (FIG. 5, described below), the portion of the parietal pericardium is manipulated by advancing the puncture device 200 so that it tents the parietal pericardium into the pericardial cavity 236. In other embodiments (FIG. 8, described below), the parietal pericardium is manipulated using suction to draw tissue of the parietal pericardium into a cannula lumen 803 in which the puncture device 200 has been positioned. The parietal pericardium tissue forms a bleb 802 that presses against the distal end of the puncture device 200.

A third step of the method is delivering energy via an energy delivery device 212 at the distal end of the puncture device 200 to puncture the parietal pericardium while maintaining the distal end of the puncture device 200 in a substantially stationary position relative to the portion of the parietal pericardium to be punctured. In some embodiments, for example when a 'bleb' is formed utilizing suction as described hereinbelow, the distal end of the puncture device remains stationary since the portion of the parietal pericardium is also being held substantially stationary about the distal end via suction (and thus the relative positions of the puncture device and portion of parietal pericardium are maintained). The stationary position is sufficiently distanced from the myocardium 228 such that the energy delivery will not damage the heart wall.

Methods comprising manipulating the parietal pericardium provide improved safety by advancing the puncture device 200 when the energy delivery is turned off and keeping the puncture device substantially stationary relative to the portion of the parietal pericardium to be punctured while energy is being delivered whereby access to the pericardial cavity is gained while avoiding advancement of the puncture device through tissue while energy is being delivered.

Some embodiments which include a step of 'tenting' further comprise the additional step, prior to advancing the puncture device 200, of advancing an elongated supporting member (cannula 224) until the elongated supporting member is positioned adjacent to the parietal pericardium. The step of advancing the puncture device 200 is accomplished by advancing the puncture device through a lumen of the elongated supporting member. In some embodiments, the energy is electrical energy, typically in the radiofrequency range.

Figure 5A:
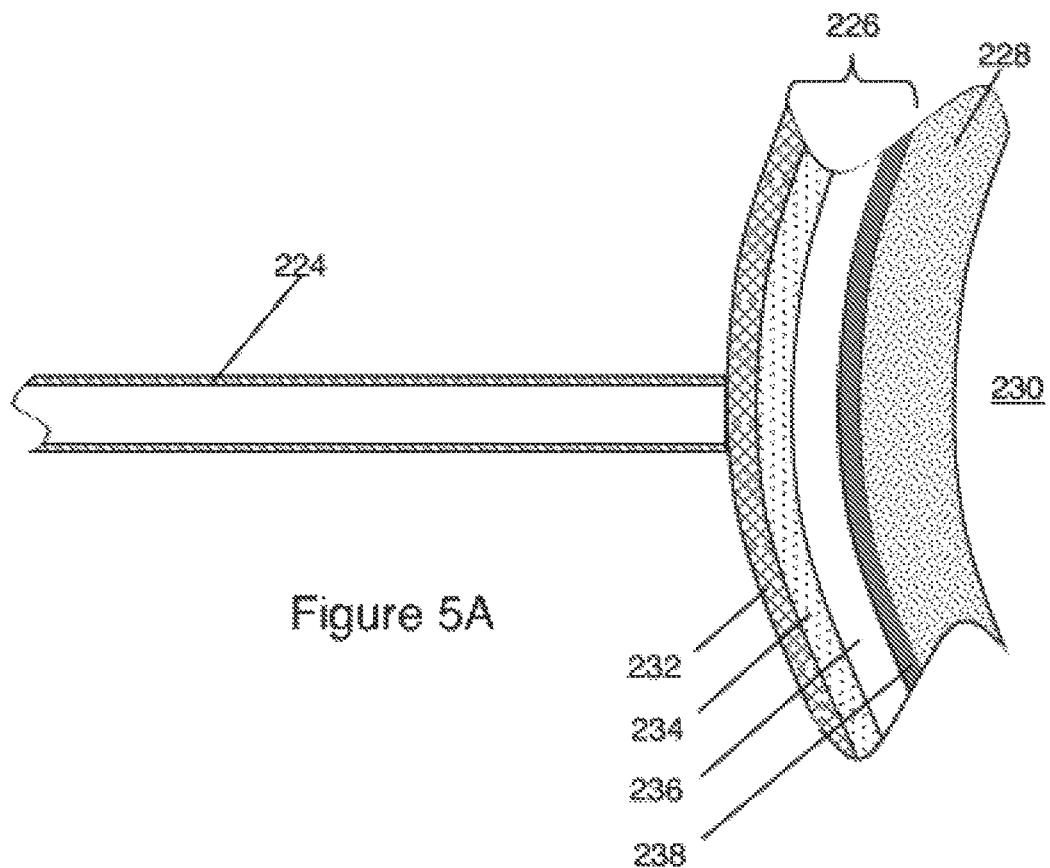
FIGS. 5A-5D are cross-sectional illustrations of the steps of an embodiment of a method of the present invention.
Figure 5B:
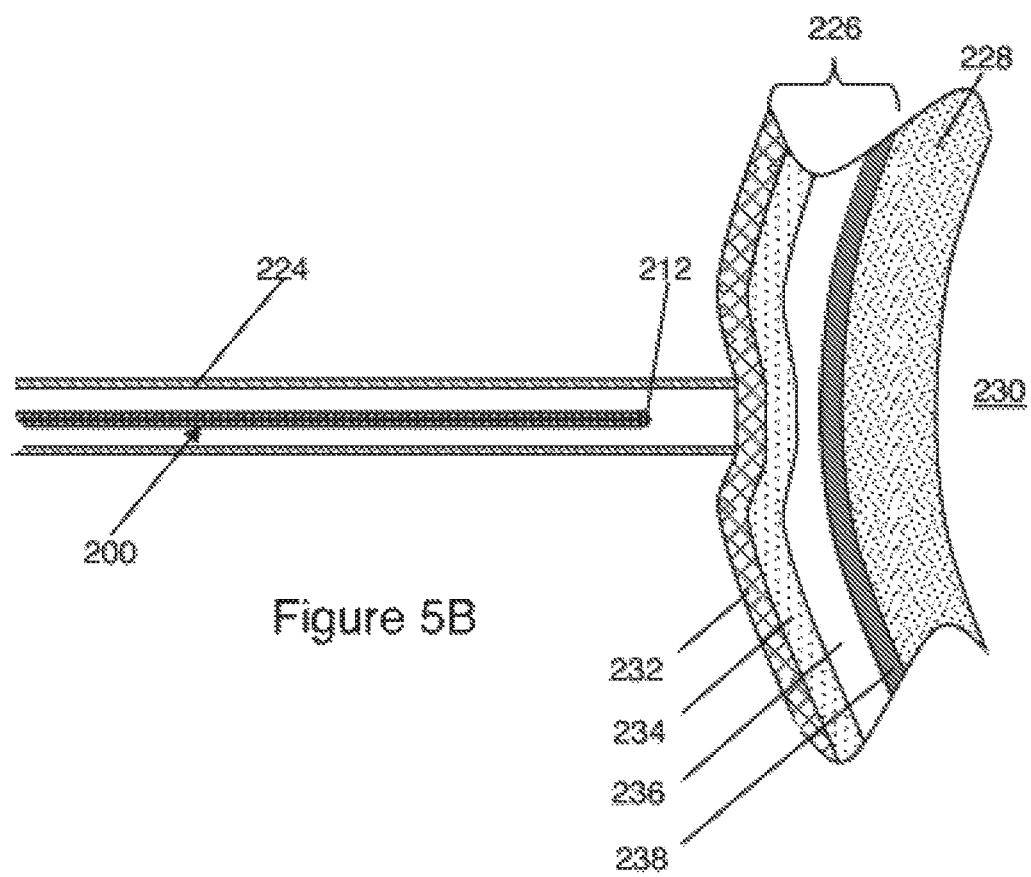
Figure 5C:
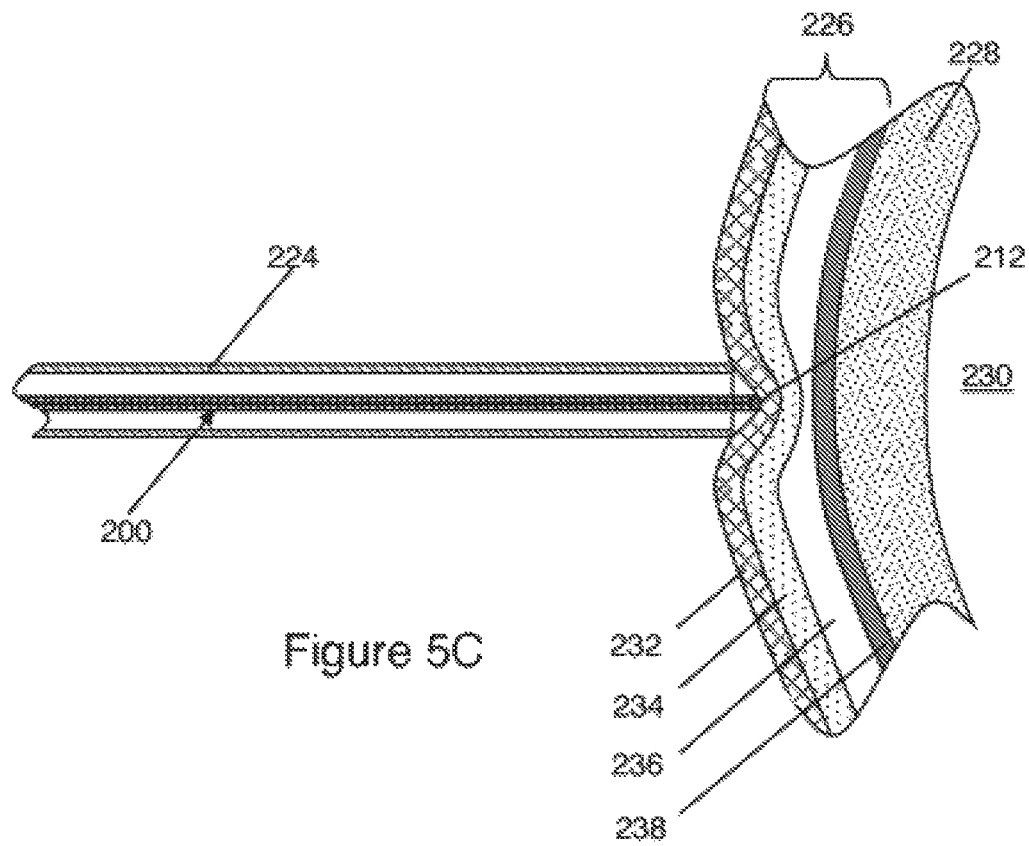
Figure 5D:
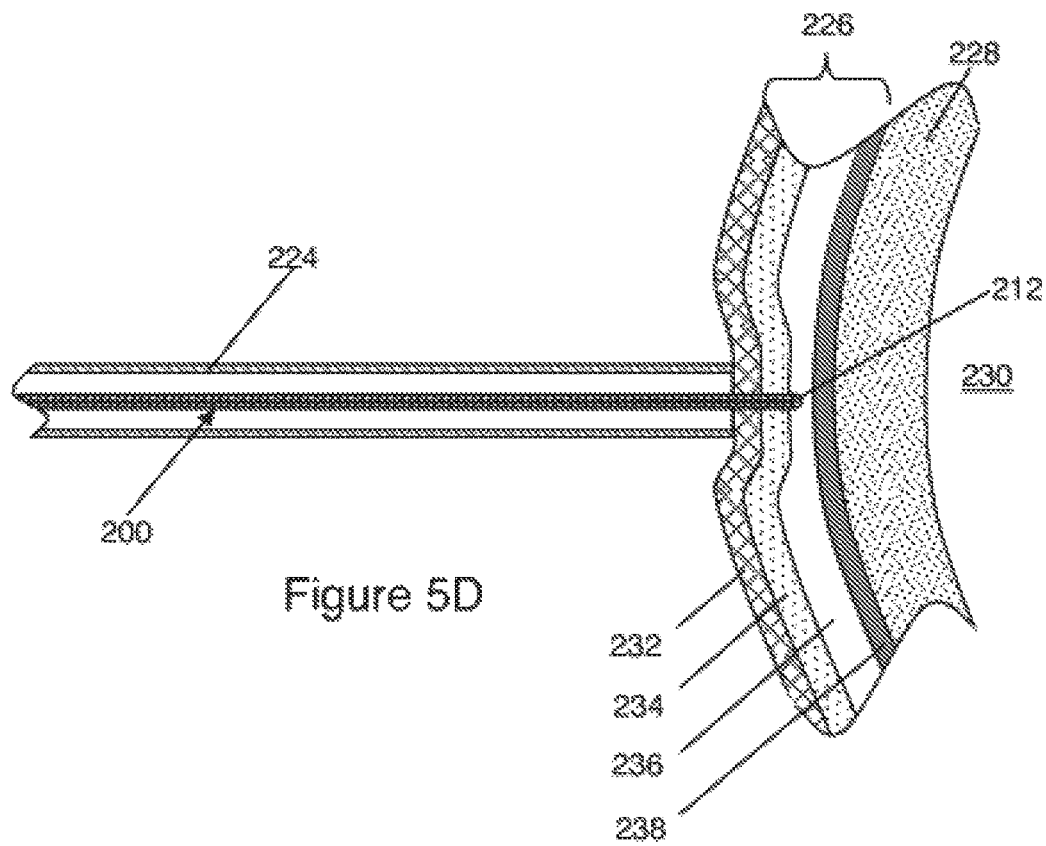

Making reference to FIGS. 5A to 5D, an embodiment of the pericardial tenting method includes the steps of: advancing an elongated supporting member (cannula 224) until it contacts the parietal pericardium (FIG. 5A) and optionally tents the parietal pericardium into the pericardial cavity (FIG. 5B shows tenting); advancing the puncture device 200 to contact an area of the parietal pericardium that is close to the supporting member and/or tented by the supporting member; further advancing puncture device 200 until the device tents or further tents the parietal pericardium into the pericardial cavity 236 (FIG. 5C); and, while keeping the puncture device substantially stationary relative to the portion of the parietal pericardium to be punctured (i.e. maintaining the pericardial portion in tension about the device), delivering energy from the energy delivery device 212 of puncture device 200 to puncture the parietal pericardium whereby the portion of the parietal pericardium that is tented by the puncture device 200 recovers over the puncture device (FIG. 5D). In some embodiments, the forward pressure of the supporting member will create tension in a tented area of the parietal pericardium. In typical embodiments of the invention, most or all of the tenting is accomplished by puncture device 200.

If the parietal pericardium (pericardium layers 232, 234) has been successfully punctured, puncture device 200 may be further advanced into the pericardial cavity without energy delivery (energy turned off). If the puncture device 200 cannot be advanced, then its position may be confirmed and more energy delivered from energy delivery device 212 to complete the puncture. In some examples of the method, an electrocardiogram may be taken to identify the tip location of puncture device 200. Some embodiments of the pericardial tenting method comprise previously described uses of dilators and sheaths.

In some embodiments, such as in the example shown in FIG. 5, the supporting member is tubular and defines a tubular member lumen, and the method comprises the puncture device 200 being advanced through the tubular member lumen.

In some embodiments, the supporting member (cannula 224) is inserted between the left border of the xiphoid process and the lower left rib, at an angle of approximately 45° towards the left scapula. In other embodiments, depending on the target location on the pericardium, the physician or user adjusts the orientation and positioning of the introducer as they see fit. Physique or body build may determine the angle of entry. Furthermore, having an angled approach improves safety over a direct (90° angle) approach as an angled approach provides a greater distance between the 3 wall of epicardium 238 and the place that puncture device 200 punctures through the parietal pericardium (i.e. with an angled approach, puncture device 200 has to travel a greater distance after entering pericardial cavity 236 to contact epicardium 238).

Previously described means for visualizing, positioning, and delivering energy may be used in conjunction with embodiments which utilize a 'tenting' procedure. For example, the distal tips of the supporting member and/or puncture device 200 may have radiopaque marker bands. In some embodiments the distal tip of the supporting member includes radiopaque filler, for example, barium sulfate, bismuth subcarbonate, and tungsten powder. Embodiments of puncture device 200 used in the method may additionally have a sideport or lateral aperture for injecting contrast fluid.

In some alternative embodiments of the pericardial tenting method, the energy is optical energy. In other alternative embodiments of the pericardial tenting method, the energy is ultrasonic energy. While typical embodiments of the method include the use of monopolar energy delivery, alternative embodiments include the use of bipolar energy delivery. Some alternative embodiments of the tenting method include the use a relatively rigid puncture device instead of a flexible device. Some alternative embodiments include the puncture device being advanced towards the pericardium outside of the supporting member.

Figure 7:
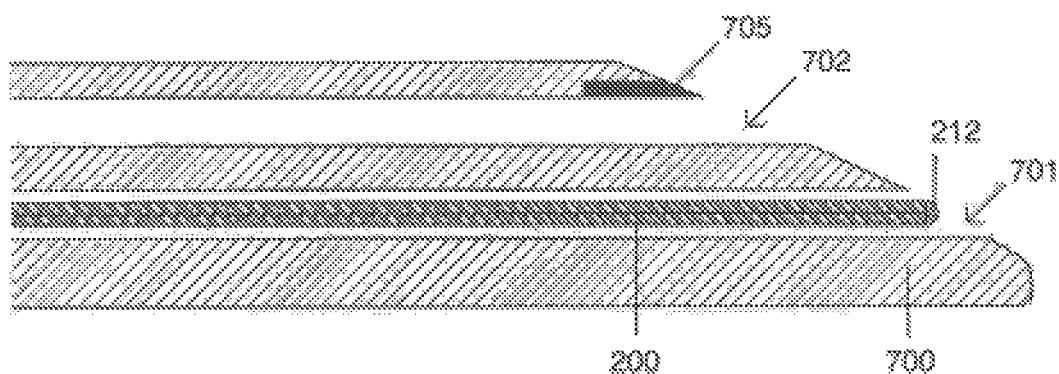
FIG. 7 is an illustration of an embodiment of an apparatus of the present invention.

Some alternative embodiments of the tenting method comprise the use of a bevelled cannula with more than one lumen. FIG. 7 illustrates a bevelled cannula 700 having a generally flattened atraumatic tip to avoid damage to the pericardium 226. Cannula 700 defines a first lumen 701 for travel of puncture device 200 therethrough and a second lumen 702 for delivering contrast fluid and/or aspirating fluid from pericardial cavity 236. Puncture device 200 includes energy delivery device 212. Some such embodiments include a return electrode to enable bipolar energy delivery, for example, electrode 705 of FIG. 7. In some embodiments, the distal tip of the supporting member (cannula 700) includes a radiopaque marker band and/or radiopaque filler.

Figure 8C:
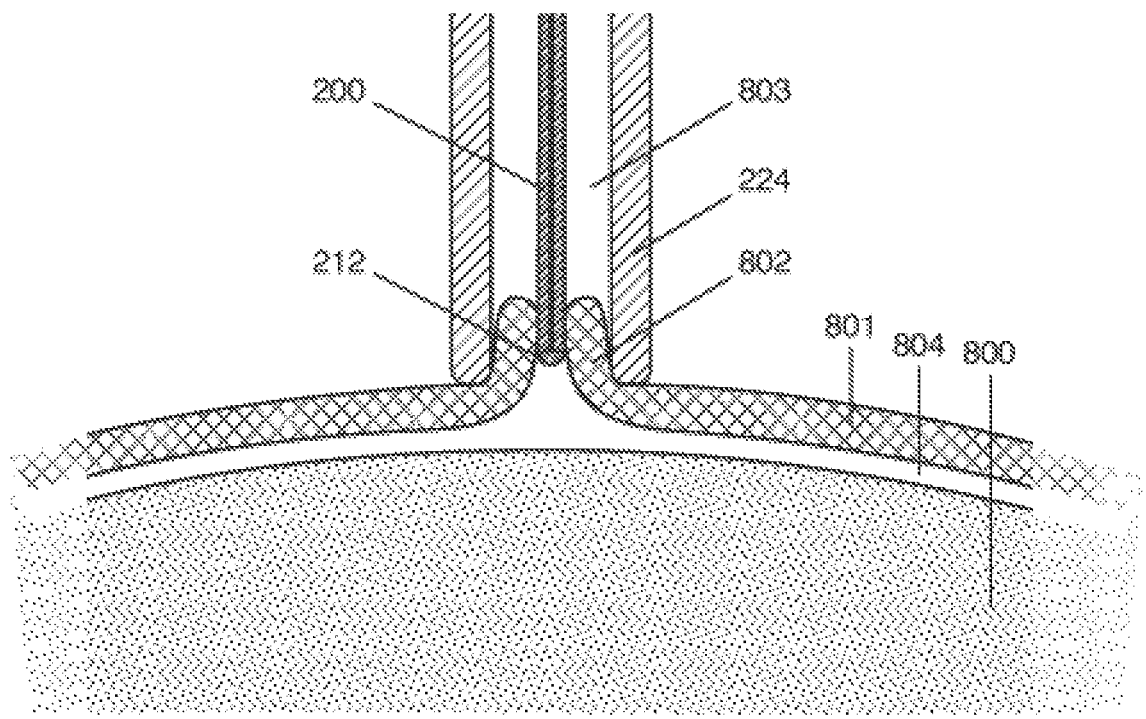

Another embodiment comprising manipulating the parietal pericardium includes using suction to pull tissue into a tube wherein a stationary puncture device (relative to the portion of the parietal pericardium to be punctured) delivers energy to puncture the parietal pericardium without damaging the myocardium. Making reference to FIGS. 8A-C, one embodiment of the method comprises: advancing a cannula 224 to abut the parietal pericardium 801 which surrounds heart tissue 800 whereby parietal pericardium 801 (which is comprised of compliant tissue matter) and cannula 224 form a seal; confirming that the position of puncture device 200 is fixed to limit or prevent longitudinal travel of the puncture device within the lumen 803 and that a distal end of puncture device 200 is positioned within the lumen about the distal end of cannula 224 (FIG. 8A); using suction to draw a portion of parietal pericardium 801 into lumen 803 to create a bleb 802 that is placed in tension around the puncture device (FIG. 8B); and delivering energy through energy delivery device 212 of a puncture device 200 to puncture bleb 802 of parietal pericardium 801, thereby providing access to the pericardial cavity 804 (FIG. 8C). Previously described means may be used to confirm access to the pericardial cavity. To prevent damage to the myocardium of heart tissue 800, in some embodiments the distal end of puncture device 200 lines up with the distal end of cannula 224, while in other embodiments the distal end of puncture device 200 is slightly recessed from (or inside) the distal end of cannula 224. Furthermore, once puncture device 200 is fixed in place and cannula 224 is situated to abut parietal pericardium 801, the method requires no movement of mechanical parts in close proximity to the heart to achieve access to the pericardial cavity 804.

In some embodiments, the distal end of cannula 224 is comprised of a compliant (yielding) material to further facilitate forming a seal with the parietal pericardium 801.

In some embodiments, the puncture device 100 has an atraumatic distal end 110 which is blunt for facilitating using ultrasound for imaging the distal end 110. A method of using such a device for accessing a pericardial cavity of a heart, comprises: (a) advancing a distal end 110 of a puncture device 100 towards the heart from a subxiphoid region of a patient wherein the distal end 110 of the puncture device 100 is atraumatic and comprises an energy delivery device 112; (b) positioning the energy delivery device 112 at a target site on a pericardium of the heart using ultrasound for imaging; and (c) delivering energy from the energy delivery device 112 to a tissue of the target site to create a channel to the pericardial cavity. Using energy delivery for puncturing (typically electrical energy) allows for distal end 110 to be blunt and not narrowed, which in turn allows for the effective use of ultrasound imaging. In contrast, the narrow and pointed end of a typical mechanical needle is not sufficiently echogenic for effective ultrasound imaging. In typical embodiments, the puncture device 100 comprises an elongate member 102 and wherein the distal end 110 of the puncture device 100 is closed. Some embodiments include the elongate member 102 defining a single lumen therethrough. Some such embodiments have a distal region 108 of the puncture device 100 which defines an aperture extending substantially radially outwardly from the lumen. Typically, the channel to the pericardial cavity is created without using suction to form a bled. This provides for maintaining constant fluid pressure within the pericardial cavity.

In some embodiments of the method, step (b) further comprises tenting the tissue of the target site so that the tissue is in tension, and wherein the puncture device 100 is used for both tenting in step (b) as well as delivering energy in step (c). To provide for increased safety, the tissue may be tented a distance less than a thickness of a ventricular wall of the heart. As previously described, the puncture may be used with a cannula which is also used for tenting.

Some embodiments of the method of using ultrasound imaging with an atraumatic puncture device 100 include using an external transducer which is placed on the outside of the patient. Some alternative methods comprise positioning an intracardiac echocardiographic imaging catheter within the heart for visualizing the position of the puncture device 100. Other alternative embodiments include positioning an esophageal probe within an esophagus of the patient for transesophageal echocardiogram (TEE) imaging of the puncture device 100. TEE includes a probe having an ultrasound transducer being placed in the patient's esophagus.

To further facilitate ultrasound imaging, the puncture device 100 may comprise an elongate member 102 having a textured surface proximal of the energy delivery device 112 and a layer of insulation covering the textured surface. The textured surface interferes with sound wave and thereby provides better ultrasound imaging than a smooth surface. The textured surface is typically on the outside of a shaft of the elongate member 102, but some alternative embodiments have a textured internal surface, with some specific alternative embodiments have a textured internal surface which defines a lumen. A textured internal surface wouldn't require a layer of insulation. Some alternative embodiments include cuts into a surface for increasing echogenicity. Details about textured and cut surfaces are described in U.S. application Ser. No. 13/962,396, entitled "Medical devices with visibility enhancing features", filed Aug. 8, 2013, and hereby incorporated-by reference in its entirety.

The atraumatic distal end 110 of the puncture device 100 typically has no sharp edges and may be a rounded tip, a hemispherical tip, a flat tip, a bullet-shaped tip, or some other blunt shape. Examples of blunt-shaped tips are described U.S. Pat. No. 8,192,425, entitled "Radiofrequency Perforation Apparatus", and incorporated herein by reference. In some embodiments, distal region 108 of puncture device 100 defines an aperture extending substantially radially outwardly from the lumen i.e. a sideport.

In some embodiments of the method of using ultrasound imaging with an atraumatic puncture device 100, step (c) comprises delivering energy more than once i.e. repeating the delivery of energy until a channel is formed substantially through said parietal pericardium. With some examples of the method, the energy is electrical energy which may be delivered in pulses and may be in the radiofrequency range. In some alternative embodiments, the energy is ultrasonic energy.

Some embodiments further comprise the steps of advancing a guidewire into the pericardial cavity through the channel and visualizing the guidewire using ultrasound imaging to confirm access to the pericardial cavity. In some such embodiments, the guidewire is advanced through a lumen of the puncturing device, while in some alternative embodiments a dilator or sheath is advanced over puncture device 100 and into the pericardial cavity, and the guidewire is advanced through the dilator or sheath. Some embodiments include using both a dilator and sheath.

Embodiments may further comprise a step of injecting a contrast fluid into the pericardial cavity through the channel to confirm that the energy delivery device 112 is at least partially within the pericardial cavity. In some such embodiments, the step of injecting a contrast fluid is performed using the puncture device 100.

Thus, embodiments of the present invention provide a method for accessing the pericardial cavity, whereby the risk of damaging the myocardium is substantially reduced. By delivering energy to create a channel through the outer layers of the pericardium to the pericardial cavity, the user may significantly reduce the risk of perforating the myocardium as may occur when using a needle with mechanical force or when employing a surgical procedure to cut the pericardium. In some embodiments, safety is further enhanced by delivering energy using a puncture device with a blunt tip which can be visualized using ultrasound. In some such embodiments, energy is delivered in pulses and/or while the puncture device remains substantially stationary relative to the portion of the parietal pericardium to be punctured.

Safety of the procedure of accessing the pericardial cavity can be further increased by using contrast fluid with the medical imaging.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

I claim:

1. A method of accessing a pericardial cavity of a heart, the method comprising the steps of: (a) advancing a puncture device towards a heart, the puncture device including an energy delivery device at a distal end of the puncture device; (b) delivering a single pulse of a pulsed energy through the energy delivery device to a parietal pericardium of the heart to create a void relatively close to the energy delivery device while maintaining the distal end of the puncture device in a substantially stationary position relative to the parietal pericardium; (c) advancing the puncture device a short distance into the void; (d) checking if the puncture device has accessed the pericardial cavity by measuring pressure on the distal end of the puncture device; and (e) repeating steps (b), (c), and (d), if necessary, until the energy delivery device is located at least partially within the pericardial cavity.

2. The method of claim 1, wherein step (c) comprises advancing the puncture device a distance greater than 0 mm and less than 1 mm.

3. The method of claim 1, wherein step (c) comprises advancing the puncture device a distance of about 1 mm.

4. The method of claim 1, wherein step (c) comprises advancing the puncture device advancing the puncture device a distance greater than 0 mm and less than 0.4 mm.

5. The method of claim 1, wherein step (c) comprises advancing the puncture device a distance of from about 0.4 mm to about 1 mm.

6. The method of claim 1, wherein step (d) comprises measuring pressure using a transducer at the distal end of the puncture device.

7. The method of claim 1, wherein the puncture device includes a lumen and an aperture at the distal end of the puncture device wherein the lumen is in fluid communication with the aperture, and step (d) comprises measuring pressure using an external pressure monitoring device which is in fluid communication with the lumen.

8. The method of claim 1, wherein step (b) comprises using monopolar energy delivery.

9. The method of claim 1, wherein step (b) comprises using bipolar energy delivery.

10. The method of claim 1, wherein step (b) comprises using pulsed optical energy.

11. The method of claim 1, wherein step (b) comprises using DC electrical energy.

12. The method of claim 1, wherein step (d) comprises injecting a contrast fluid such that the contrast fluid can be seen surrounding a cardiac silhouette.

13. The method of claim 1, wherein step (d) comprises aspirating fluid.

14. The method of claim 1, further comprising visualizing a position of a cannula using medical imaging, the cannula defining a lumen for receiving the puncture device.

15. The method of claim 14, further comprising positioning the cannula adjacent to a surface of a fibrous pericardium, using medical imaging.

16. The method of claim 15, further comprising positioning the energy delivery device at a distal end of the lumen of the cannula, prior to delivering energy.

17. The method of claim 1, further comprising plotting an electrocardiogram to confirm a position of the energy delivery device.

18. The method of claim 1, further comprising identifying contact between the energy delivery device and a tissue of the heart using an electrical impedance.

* * * * *